(12) United States Patent
Liu et al.

(10) Patent No.: US 6,682,701 B1
(45) Date of Patent: Jan. 27, 2004

(54) LARGE CAPACITY ACID OR BASE GENERATOR APPARATUS

(75) Inventors: Yan Liu, Santa Clara, CA (US); Hamish Small, Leland, MI (US); Nebojsa Avdalovic, San Jose, CA (US)

(73) Assignee: Dionex Corporation, Sunnyvale, CA (US)

( * ) Notice: Subject to any disclaimer, the term of this patent is extended or adjusted under 35 U.S.C. 154(b) by 563 days.

(21) Appl. No.: 09/612,074

(22) Filed: Jul. 7, 2000

Related U.S. Application Data

(62) Division of application No. 09/017,050, filed on Feb. 2, 1998, now Pat. No. 6,225,129.

(51) Int. Cl.[7] .............................................. G01N 30/02
(52) U.S. Cl. ........................ 422/99; 422/70; 422/82.02; 436/150; 436/161; 436/174; 210/198.2; 73/61.53; 73/61.55; 73/61.56; 204/551; 204/647; 205/335; 205/628; 205/633; 205/637
(58) Field of Search ................................. 436/161, 174, 436/150; 422/70, 82.02, 99; 210/656, 670, 681, 198.2, 263, 269; 73/61.53, 61.55, 61.56; 204/551, 647; 205/335, 633, 637, 628

(56) References Cited

U.S. PATENT DOCUMENTS

| | | | |
|---|---|---|---|
| 4,806,215 A | | 2/1989 | Twardowski |
| 5,045,204 A | * | 9/1991 | Dasgupta et al. ........... 210/635 |
| 5,198,086 A | | 3/1993 | Chlanda et al. |
| 5,567,293 A | | 10/1996 | Paleologou et al. |
| 5,759,405 A | * | 6/1998 | Anderson et al. ........... 210/656 |

* cited by examiner

*Primary Examiner*—Jan Ludlow
(74) *Attorney, Agent, or Firm*—Dorsey & Whitney LLP; David J. Brezner

(57) ABSTRACT

Method and apparatus for generating an acid or base, e.g. for chromatographic analysis of anions. For generating a base the method includes the steps of providing a cation source in a cation source reservoir, flowing an aqueous liquid stream through a base generation chamber separated from the cation source reservoir by a barrier (e.g. a charged membrane) substantially preventing liquid flow while providing a cation transport bridge, applying an electric potential between an anode cation source reservoir and a cathode in the base generation chamber to electrolytically generate hydroxide ions therein and to cause cations in the cation source reservoir to electromigrate and to be transported across the barrier toward the cathode to combine with the transported cations to form cation hydroxide, and removing the cation hydroxide in an aqueous liquid stream as an effluent from the first base generation chamber. Suitable cation sources include a salt solution, a cation hydroxide solution or cation exchange resin.

9 Claims, 29 Drawing Sheets

LARGE CAPACITY ACID OR BASE GENERATOR APPARATUS

CROSS-REFERENCE TO RELATED APPLICATION

This is a divisional of application Ser. No. 09/017,050 filed Feb. 2,1998 now U.S. Pat. No. 6,225,129.

Reference is made to co-pending H. Small, et al. U.S. patent application Ser. No. 08/783,317, filed Jan. 15, 1997.

BACKGROUND OF THE INVENTION

The present invention relates to a large capacity apparatus for generating a high purity acid or base particularly for use as a chromatography eluent, and to a method of using the apparatus.

In liquid chromatography, a sample containing a number of components to be separated is directed through a chromatography separator, typically an ion exchange resin bed. The components are separated on elution from the bed in a solution of eluent. One effective form of liquid chromatography is referred to as ion chromatography. In this known technique, ions to be detected in a sample solution are directed through the separator using an eluent containing an acid or base and thereafter to a suppressor, followed by detection, typically by an electrical conductivity detector. In the suppressor, the electrical conductivity of the electrolyte is suppressed but not that of the separated ions so the latter may be detected by the conductivity detector. This technique is described in detail in U.S. Pat. Nos. 3,897,213, 3,920,397, 3,925,019 and 3,956,559.

There is a general need for a convenient source of high purity acid or base for use as an eluent for liquid chromatography and, particularly, for ion chromatography. In one technique, described in U.S. Pat. No. 5,045,204, an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

There is a particular need for a pure source of acid or base which can be generated at selected concentrations solely from an ion exchange bed without the necessity of an independent reservoir of an acid or base starting aqueous stream. There is a further need for such a system which can be continuously regenerated. Such need exists in chromatography, and specifically ion chromatography, as well as other analytical applications using acid or base such as in titration, flow injection analysis and the like.

SUMMARY OF THE INVENTION

In copending application Ser. No. 08/783,317, filed Jan. 15, 1997, a method and apparatus is described for generating acid or base in an aqueous stream, such as water alone or in combination with additives (e.g., ones which react with the acid or base or with the sample). The system provides an excellent source of high purity acid or base for use as an eluent for chromatography and, particularly, ion chromatography. The present system is an improvement over the one described in the copending application.

Referring first to the present system in which a base is generated e.g. for chromatographic analysis of anions, the method includes the steps of:

(a) providing a cation source in a cation source reservoir, (b) flowing an aqueous liquid stream through a base generation chamber separated from the cation source reservoir by a barrier substantially preventing liquid flow while providing a cation transport bridge, (c) applying an electric potential between an anode in electrical communication with said cation source reservoir and a cathode in electrical communication with the base generation chamber to electrolytically generate hydroxide ions in the base generation chamber and to cause cations in the cation source reservoir to electromigrate toward said first barrier and to be transported across the barrier toward the cathode to combine with the transported cations to form cation hydroxide, and (d) removing the cation hydroxide in an aqueous liquid stream as an effluent from the first base generation chamber.

Suitable cation sources include a salt solution or a cation hydroxide solution which can be supplied to the cation source reservoir by pumping from a remote reservoir. The solution can be recycled to the remote reservoir. Also, the cation source may comprise a cation exchange bed, e.g., resin particles in a stationary bed or suspended in an aqueous liquid, alone or in combination with the salt solution.

The method may also be used for generating an acid, e.g. for use as an eluent for chromatographic analysis of cations by reversing the charges of the ion source, the barrier, the electrical potential and any other charged components of the system.

Another embodiment of the invention is an apparatus for generating an acid or base including:

(a) an ion source reservoir of either anions or cations, (b) an acid or base generation chamber having inlet and outlet ports, (c) a first barrier between the ion source reservoir and the acid or base generation chamber, substantially preventing liquid flow while providing an ion transport bridge for only ions of one charge, positive or negative, (d) a first electrode in electrical communication with the ion source reservoir, (e) a second electrode in electrical communication with the first acid or base generation chamber, and (f) an aqueous liquid source in fluid communication with the acid or base generation chamber inlet port.

The apparatus can be used to supply the generated acid or base to a chromatography system or any other analytical system which uses a high purity acid or base.

DETAILED DESCRIPTION OF PREFERRED EMBODIMENTS

Figure 1:
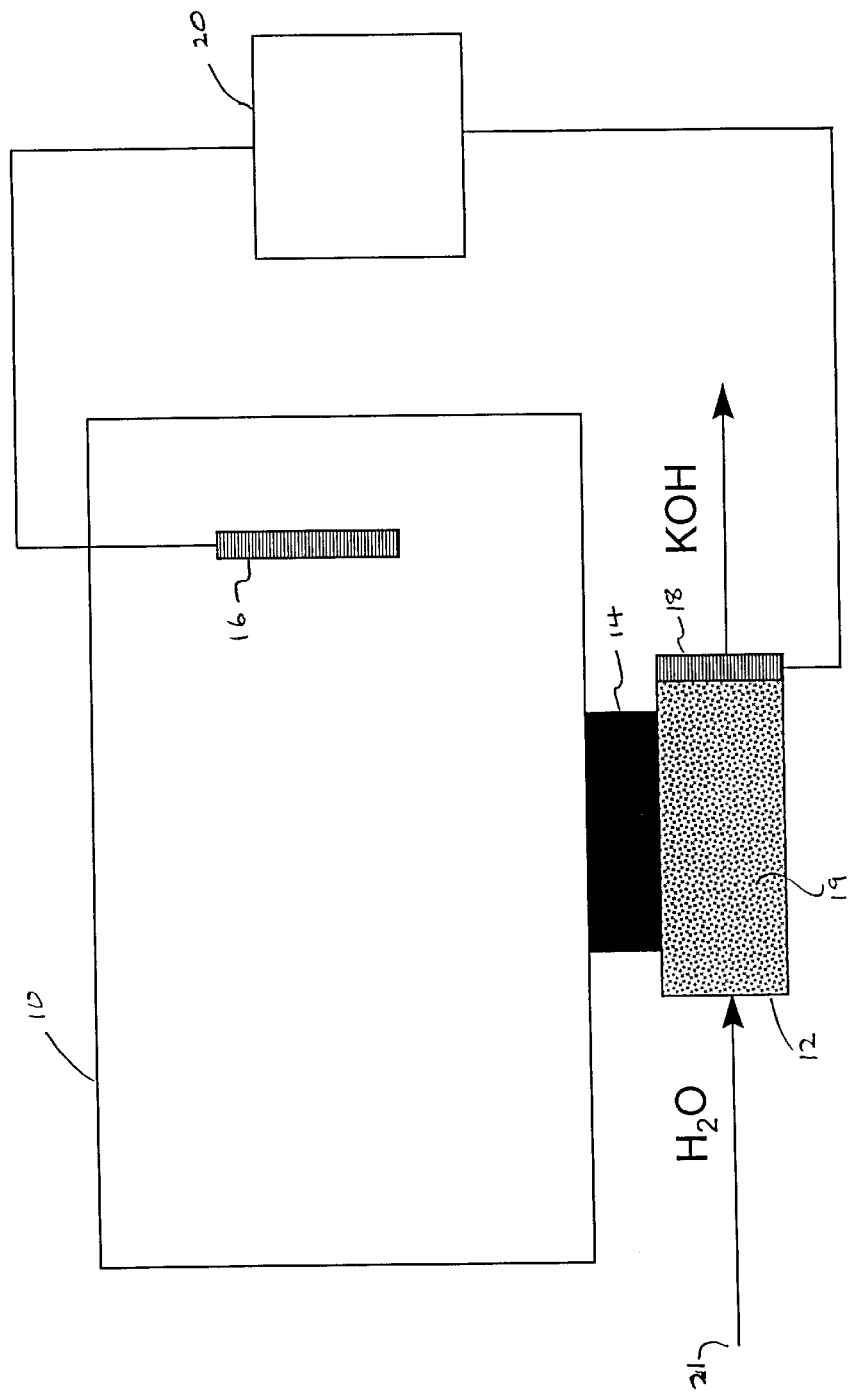
FIGS. 1–8 and 10–12 are schematic representations of apparatus according to the present invention.

The system is applicable to the generation of eluent for liquid chromatography forms other than ion chromatography. For example, it is applicable to liquid chromatography using an ultraviolet (UV) detector. The eluent may be in a form (e.g. salt) other than a pure acid or base. Thus, the term "aqueous stream" includes pure water or water with such additives. Also, the terms "eluent comprising a base", "eluent comprising an acid", an "acid" or a "base" mean an aqueous stream including acid or base generated according to the invention regardless of the form it takes on mixing with other reagents present in the aqueous stream. As used herein, the term "cation" excludes hydronium ion and the term "anion" excludes hydroxide ion. The system is also applicable to other non-chromatographic analytical systems which use a high purity acid or base.

The copending application uses some of the same principles as the present invention and its disclosure is incorporated by reference. Such disclosure includes a high purity solution of acid or base electrochemically generated by passing deionized water through an electrically polarized bed of ion exchange resin in the desired ionic form placed between two electrodes. For example, in the generation of a KOH solution, deionized water is pumped through a column packed with a cation exchange resin in $K^+$ form, and a DC voltage is applied between the anode at the column inlet and the cathode at the column outlet. The electrochemical reaction at the anode generates $H^+$ ions by splitting water. Under the influence of the electrical field, $H^+$ ions electromigrate into the resin bed to displace $K^+$ ions, which in turn migrate downstream through the resin bed and combine with $OH^-$ ions generated at the cathode to produce KOH. The concentration of KOH generated is determined by the electrical current applied and the flow rate of the deionized water through the column. Similarly, a high purity acid (e.g., methanesulfonic acid) solution can be generated using a generation column containing an anion exchange resin in the desired ionic form.

The acid or base generation column described above is an attractive source of high purity eluent for ion and liquid chromatography for a number of reasons. For example, chromatographic separations can be conveniently performed using only deionized water as the carrier. Since acid or base is generated on-line, the need of often-tedious, off-line preparation of eluents can be eliminated. Second, the eluent strength (the concentration of acid or base) can be controlled precisely and conveniently by controlling the electrical current applied to the acid or base generation column and the flow rate. Third, gradient chromatographic separations can be accomplished with current gradients and a less costly isocratic pump instead of using a more expensive gradient pump. Fourth, the use of an acid or base generation column can improve the performance of chromatographic methods, since the eluent generated on-line can be free of contaminants that are often introduced if it is prepared off-line by conventional means. For example, the presence of carbonate in hydroxide eluent due to sorption of carbon dioxide from air often seriously compromises the performance of an ion chromatography method; this problem will be eliminated by using the high purity hydroxide eluent generated on-line. Fifth, the reliability of the chromatography pumping system can be improved, the lifetime of pump seal can be extended significantly since the pump is used to pump deionized water instead of more corrosive acid or base solution. These same advantages and principles apply to the present invention. In addition, the present invention retains the advantages of the acid or base generation column, and provides a significant improvement in the generation of high purity acid or base solutions for an extended period of time for ion and liquid chromatography, and other applications.

The method and apparatus for generation of acid or base according to the present invention will first be described to supply eluent, e.g., for ion chromatography. Although applicable to anion or cation analysis, the system will be described for generation of a base suitable for use as an eluent in the analysis of anions on an ion exchange resin packed bed form. In this instance, the cation exchange bed generates a base such as an alkali metal hydroxide, typically sodium or potassium. For analysis of cations, the eluent generated is an acid such as methanesulfonic acid. The system will first be described for the generation of KOH as the base.

FIG. 1 schematically illustrates a general form of a large capacity base (KOH) generator form according to the present invention. The apparatus includes cation ($K^+$) ion source reservoir 10. As will be explained in more detail below, the cation source may be a cation-containing solution such as a salt solution or a cation hydroxide solution. Alternatively, the cation source may be a cation exchange bed including exchangeable cations of the type which form a cation hydroxide. The bed may be formed of ion exchange resin particles in a fixed or stationary bed or suspended particles in an aqueous liquid. A gas vent may be provided in reservoir 10 to vent oxygen generated therein as described hereinafter.

Base generation chamber 12 is separated from the ion source reservoir 10 by a barrier 14, suitably in the form of a charged perm-selective membrane described below. Charged barrier 14 substantially prevents liquid flow while providing an ion transport bridge for cations from the ion source reservoir 10 to base generation chamber 12. As used herein, the term "barrier" refers to the charged material (e.g. membrane) separating reservoir 10 and chamber 12 which permits ion flow but blocks liquid flow, alone or in combination with an appropriate flow-through housing in which the barrier is mounted transverse to flow across the entire flow path.

The charged barrier 14 should be of sufficient thickness to withstand the pressures in chamber 12. For example, if chamber 12 is on line with a chromatography system, such pressures may be on the order of 1,000 to 3,000 psi. When using a membrane as barrier 14, it is suitably configured of circular cross-section within a cylindrical external short column. Typical dimensions for the membrane are about 4–6 mm diameter and 1–3 mm in length. The barrier can be fabricated by stacking multiple disks of cation membranes together within the cylindrical column. Alternatively, barrier 14 can be prepared from a single ion exchange membrane of appropriate thickness or a block or rod of appropriate ion exchange material which permits passage of the potassium but not of the liquid.

An anode 16 is disposed in electrical contact with, and preferably within, cation source reservoir 10 and a cathode 18 is disposed in electrical contact with, and preferably within, base generation chamber 12. A suitable DC power supply 20 connects the anode and the cathode. Also, there is a continuous electrical path from anode 16 through barrier 14 to cathode 18. Aqueous stream 20, suitably deionize water, flows through an inlet port, not shown, in base generation chamber 12. KOH is generated in base generation chamber 12 and flows out of outlet port, not shown. A cation exchange resin bed 19 (e.g. in $K^+$ form) can be packed in chamber 12 in contact with barrier 14 and cathode 18 to provide good electrical contact therebetween. As illustrated, the flow of aqueous stream 20 is toward cathode 18. However, if desired, the flow may be in the opposite direction.

For the production of pure base (e.g. KOH), high-purity deionized water from source 21 is pumped to generation chamber 12. Water splitting takes place at both electrodes. The anode reaction in reservoir 10 is as follows:

$$H_2O - 2e^- \rightarrow 2H^+ + 1/2 O_2 \qquad (1)$$

During this reaction, hydronium ions are produced in reservoir 10 for the resin form of the invention, the hydronium ions pass into the cation exchange resin by electromigration displacing the exchangeable cations (e.g. $K^+$ ions) ahead of them. This displacement takes place along the length of the bed and the $K^+$ ions pass through barrier 14 into chamber 12 eventually leading to production of base (KOH) in the flowing aqueous stream in generation chamber 12. The hydroxide ions are produced in the following cathodic reaction.

$$2H_2O + 2e^- \rightarrow 2H^+ + 1/2 O_2 \qquad (2)$$

In one form of reservoir 10, the cation source is a cation-containing solution, suitably either a salt solution or a cation hydroxide solution (e.g. KOH). If a salt solution is used, it is preferably of a weakly acidic anion salt such as $K_2HPO_4$ to bind the hydronium ions produced at the anode. In this manner, $K^+$ is the primary ion passing through barrier 14, thereby minimizing the flow of $H^+$ ions. The hydronium ion generation in the reservoir provides electrical neutrality to the solution in the reservoir as the $K^+$ ions are driven across the barrier.

Figure 2:
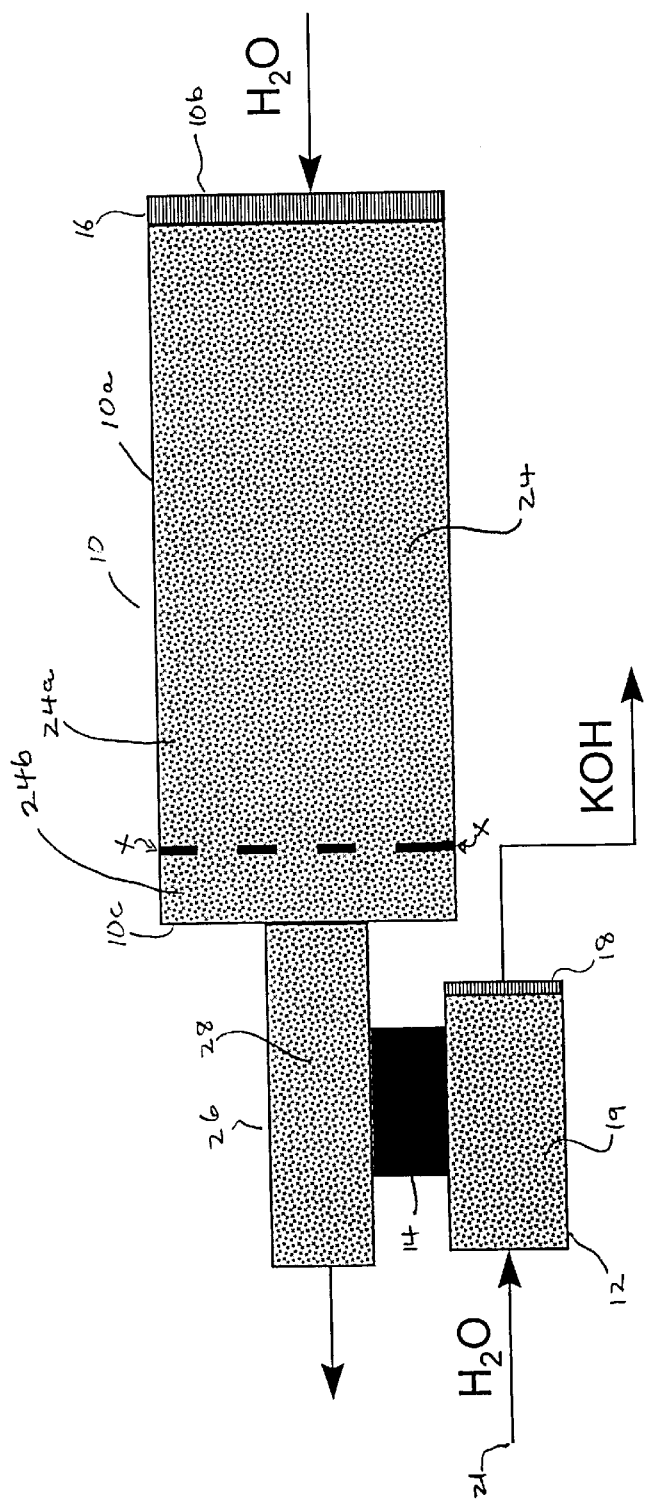

Another embodiment of the invention is illustrated in FIG. 2. This device is specifically adapted for use with an ion exchange resin form of cation source in reservoir 10. Because of the similar components in FIGS. 1 and 2, like parts will be designated with like numbers. The illustrated reservoir 10 is suitably in the form of a solid horizontal hollow cylinder 10a with inlet and outlet walls 10b and 10c, respectively, and packed with cation exchange resin in $K^+$ form. Alternative shapes, e.g. rectangular, of reservoir 10 may be used. An aqueous stream, suitably dionized water, is pumped through an inlet port, not shown, into reservoir 10. Similarly, a preferred housing for chamber 12 is a cylindrical column defining a cylindrical chamber. Thus, the terms "chamber" and "column" will be used interchangeably for chamber 12. Anode 16 is illustrated as a perforate disk disposed at the inlet side of reservoir 10 adjacent inlet wall 10b. Flow-through cation exchange resin bed 24 is suitably of similar ion exchange and flow characteristics to a chromatographic separation bed.

A preferred form of ion exchange resin bed in reservoir 10 is a "dual-bed" including a long section 24a of a strongly acidic cation exchange resin (e.g. a sulfonated resin such as sold under the trademarks Dowex 50WX8 resin or Dionex ASC resin) in $K^+$ form adjacent at the line X—X to a shorter section of a weakly acidic cation exchange resin (e.g. a carboxylate resin such as sold under the trademarks Dionex CS12A resin or Bio-Rex 70 resin) in $K^+$ form downstream at its outlet end. As used herein, "weakly acidic" anion means an anion with an acid dissociation constant (pKa) of greater than 3.0 and "strongly acidic anion" means an anion with a pKa less than about 3.0. Preferably the strongly acidic section 24a is at least about 10 percent of the length or volume of reservoir 10 and more preferably at least about 90 percent of the length or volume. Alternatively, if desired, the entire bed 24 may be formed of strongly acidic cation exchange resin.

The dual-bed approach increases the useful capacity of a KOH generator column. Once $H^+$ ions reach the bed of the weakly acidic resin, migration of $H^+$ through the resin bed is significantly slowed down because of its higher affinity to the weakly acidic functional groups. On the other hand, the migration of $K^+$ ions through the resin bed is not significantly reduced.

Therefore, more $K^+$ ions are able to reach the cathode to form KOH before the arrival of $H^+$ ions at the cathode, and thus the useful capacity of the KOH generator column is increased. In the dual-bed once $H^+$ ions reach the weakly acidic resin bed, the applied voltage needed to maintain the constant current will increase due to the development of the less conductive protonated zone in the weakly acidic resin bed.

One function of barrier 14 is to permit use of a very large reservoir 10 (e.g. 1–2 liters) supplying $K^+$ ions to generation chamber 12. This large capacity reservoir permits a long term supply of $K^+$ ions. By way of example, a typical KOH generation chamber may have a volume on the order of less than 100 μL and more typically from 100 μL to 1,000 μL. Suitable dimensions for a cylindrical shape are 4–7 mm ID and 10–50 mm in length. This facilitates use on line in a chromatography system. In contrast, reservoir 10 may be many times larger than the volume of the generation chamber 12. For example, the ratio between reservoir 10 and chamber 12 may be at least 5:1 to 10:1 or 20:1 or even higher.

Another function of barrier 14 is that it provides a high pressure physical barrier that insulates the relatively low pressure $K^+$ ion supply reservoir 10 from the generation chamber 12 which is of substantially high pressure when it is on line with a high pressure chromatography system. For example, even a very low pressure chromatography system would be pressurized to at least about 50 psi. Assuming the reservoir's atmospheric pressure (14.7 psi) the pressure maintained in the base generation chamber 12 is at least about three times the pressure maintained in reservoir 10. This isolation is particularly useful when that pressure ratio is at least about 2:1 and is even more so when the ratio is much higher, for example at least about 5:1 to at least about 10:1 to 100:1 or higher.

Because it is operated under low pressure, a large $K^+$ ion supply column can be prepared and operated safely without demanding pressure constraint. A large $K^+$ ion supply column can contain a sufficient amount of cation exchange resin in $K^+$ form to generate KOH over an extended period of time. For example, a 10-cm ID×20-cm length $K^+$ ion supply column has an internal volume of 1570 mL and can contain 2670 meq of $K^+$ ions (calculated using the resin capacity of 1.7 meg/mL). If the KOH generator column is used to generate 20 mM KOH at 1.0 mL/min, its theoretical capacity is 2225 hours, and an actual useful time is expected to be more than 1300 hours, assuming 60 percent of the total $K^+$ ion capacity is ultimately utilized for the generation of KOH.

To step down from the large volume reservoir 10 to the smaller size base generation chamber 12, an adapter section in the form of hollow cylindrical column 26 packed with cation exchange resin 28 may be disposed in open communication with column 10 through an opening in the end wall 10c of reservoir 10. Barrier 14 is disposed between cylinder 26 and generation chamber 12. A suitable configuration of barrier 14 is a hollow cylinder transverse to cylinder 26 with a barrier disk (e.g. permselective membrane) across the flow path therebetween. Generation chamber 12 also is suitably is in the form of a hollow cylinder.

Barrier 14 is suitably in the form of a stack of cation exchange membranes or a plug which prevents any significant liquid flow but permits transport of the $K^+$ ions into chamber 12. A suitable form of membrane is supplied by Membrane International of Glenrock, New Jersey (designated CMI-7000 cation exchange membrane). As illustrated, cathode 18 is a porous disk disposed adjacent to and coextensive with the end wall at the exit of chamber 14. As in the embodiment of FIG. 1, water is supplied to an inlet port of chamber 12. The KOH generated near cathode 18 exits from the outlet of chamber 12. This is advantageous as the $H_2$ gas generated at the cathode is readily swept out of chamber 12.

Anode 16 and cathode 18 disposed in reservoir 10 and generation chamber 12, respectively, can take the different forms such as porous disks, frits, rings, screens, sheets, and probes so long as they provide good contact (preferably direct contact) with the ion source or ion exchange resin. For example, the anode is preferably in direct contact with the ion exchange resin, if used, or with the solution in the reservoir if no ion exchange resin is used. Similarly, the cathode should be in direct contact with the ion exchange resin when used in the generation chamber. The electrode may also be formed by crumpling and forming a length of fine platinum wire to form a roughly disk-shaped object that allows easy flow through the structure. The electrodes are preferably made of inert material, such as platinum. In the embodiments described above, it is preferable that the electrodes be placed in a region near the outlet of generation chamber 12, although other locations may be used as well.

In another form of the electrodes, not shown, a thin inert electrically conductive screen is wrapped partially or totally around a bed of ion exchange resin in chamber 12 in a case-like configuration. This electrode design provides good contact between the cation exchange resin and the electrode surface, thus lowering the device operating voltage. Thus, higher currents can be applied to generate higher concentrations without being limited by possible excessive heating.

In general, the method of the present invention using the embodiment of FIG. 2 is performed as follows. The cation source is provided by the combination of cation exchange resin 24 in reservoir 12 and cation exchange resin 28 in column 26. The $H^+$ ion formed near anode 12 drives the $K^+$ ions through the resin until they transport across barrier 14. The $H^+$ ions produce electrical neutrality to reservoir 10. The $K^+$ ions travel across barrier 14 into chamber 12 towards cathode 18 and combines with the hydroxide ions formed at the cathode to form KOH. The aqueous stream flowing through base generation chamber 12 carries the KOH in solution for subsequent use in the analytical system.

When using a packed ion exchange bed in reservoir 10 or generation chamber 12, the higher the cross-linking of a resin the higher its capacity (expressed as milliequivalents per ml. of column); therefore, higher cross-linked resins give more compact generators. This is desirable. However, the higher the cross-linking of a resin, the less it deforms when packed in a column. Some deformation is desirable in that it improves the area of contact between resin beads thus lowering the electrical resistance of the packed bed. Lower resistance means that a particular level of current may be attained at a lower applied voltage; this, in turn, leads to less heating of the bed while carrying current, a desirable feature.

Bead deformation is favored by lowering the degree of cross linking. But, resin of very low cross-linking (say 1 to 2%) is so deformable that at certain flow rates the deformation can lead to undesirably high pressure across the bed. In summary, a wide range of cross-linking can be used. Resins of moderate cross-linkage are to be preferred, typically in the range of 4 to 16% divinyl benzene for styrene divinyl benzene polymer beads.

Other forms of ion exchange beds can be used such as a porous continuous structure with sufficient porosity to permit flow of an aqueous stream at a sufficient rate for use as an eluent for chromatography without undue pressure drop and with sufficient ion exchange capacity to form a conductive bridge of cations or anions between the electrodes. One form of structure is a porous matrix or a sponge-like material with a porosity of about 10 to 50% permitting a flow rate of about 0.1 to 3 ml/min without excessive pressure drop. Another suitable form is a roll of ion exchange film (e.g. in a configuration of such a roll on a spindle disposed parallel to liquid flow). Electrodes would be placed at each end of the roll which could be textured to provide an adequate void channel.

The aqueous stream flowing through chamber 12 may be high-purity deionized water. However, for use in some forms of chromatography, it may be desirable to modify the source with an additive which reacts with the base generated in electrode chamber 12 to produce eluents of varying potency. For the production of base, some well known additives include a source of carbonic acid, phenol, cyanophenol, and the like. (For the production of acid, such additives include m-phenylene diamine, pyridine, lysine and amino propionic acid.)

It is preferable to control the concentration of base produced in base generation chamber 12. To do so, the current, directly related to concentration, is controlled. A feed-back loop may be provided to assure sufficient voltage to deliver the predetermined current. Thus, the current is monitored when the resistance changes, and the potential is correspondingly changed by the feed-back loop. Therefore, the voltage is a slave to the reading of the current. Thus, it is preferable to supply a variable output potential system of this type (e.g., sold under the designation Electrophoresis Power Supply EPS 600 by Pharmacia Biotech and Model 220 Programmable Current Source by Keithley).

The current (voltage) requirements of a generator depend on (a) the eluent strength required; (b) the diameter of the column; (c) the length of the column; (d) the electrical resistance of the resin; and (e) the flow rate of the aqueous phase.

Figure 3:
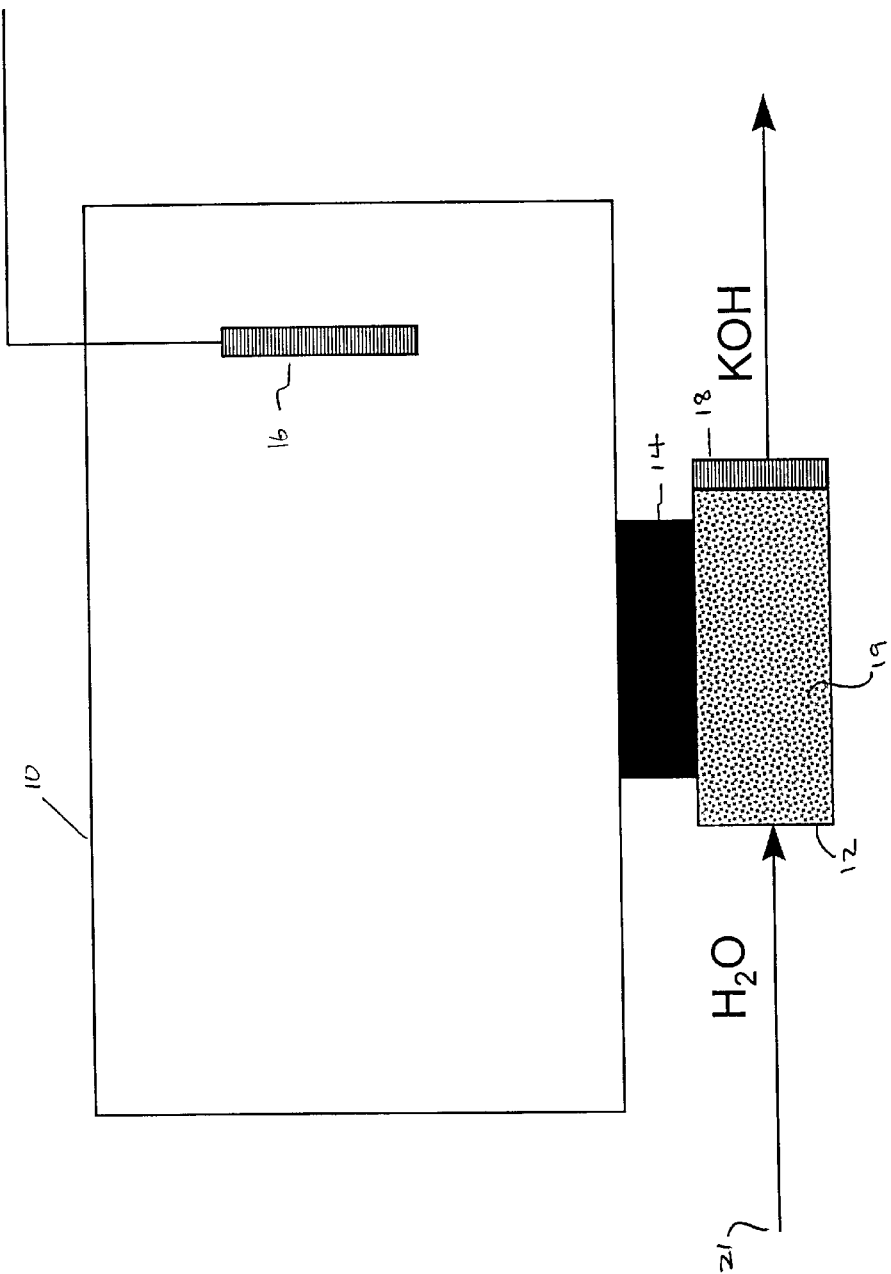

FIG. 3 illustrates another embodiment of the invention. In this instance, no ion exchange resin is used in reservoir 10. Instead, a solution of a potassium salt such as $K_2HPO_4$ is employed. Alternatively, for specific applications, KOH may be used. The potassium salt solution may be used in combination with a cation exchange resin in $K^+$ form either in a fixed resin bed or in a bed in which the resin particles are suspended in the solution. The concentration of $K^+$ ions in solution is preferable about 1 to 2 M or higher so that there is a sufficient amount of $K^+$ ions for the generation of KOH over an extended time. However, if desired, the potassium salt solution containing $K^+$ ions at lower concentrations (e.g. 0.1 to 0.5 M) can be used for specific applications. It is preferable that the anion of the potassium salt not be oxidized by the anode. It is preferable to use a potassium weakly acidic anion (e.g., $HPO_4^{2}$ or $CO_3^{2-}$) with an acid dissociation constant ($pK_a$) of 5 or higher so that the concentration of free $H^+$ ions in the solution is kept lower than 0.1 mM. $H^+$ ions, like $K^+$ ions, can migrate across barrier 14 into generation chamber 12. If such $H^+$ migration occurs in significant amounts, the direct linear relationship between the applied current and the concentration of KOH generated can be lost because $H^+$ ions can be combined with $OH^-$ ions generated at the cathode to form water and thus the performance of the system can be compromised. By using the K$_2$HPO$_4$ salt, the following reaction occurs using H$^+$ generated at anode 16 in equation (1) above.

$$2H^+ + 2HPO_4^{2-} = 2H_2PO_4^- \quad (3)$$

As in the embodiments of FIGS. 1 and 2, an aqueous stream is pumped through the generation chamber at 12 and a DC voltage is applied between anode 16 and cathode 18. K$^+$ ions migrate from reservoir 10 into generation chamber 12 through barrier 14 in the same manner described above. Also, as set out above, barrier 14 provides a high-pressure physical barrier that prevents liquid leakage and diffusion of any ions from reservoir 10 into generation chamber 12.

One advantage of this embodiment in which a solution without resin is used in reservoir 10 is that the potassium salt (e.g., K$_2$HPO$_4$) is a less expensive source of K$^+$ ion than ion exchange resin with exchangeable K$^+$ ions. Also, it is easier to replenish the reservoir with a fresh source of potassium salt. By way of example, in the embodiment of FIG. 3 using a one liter reservoir filled with 2.0 M K$_2$HPO$_4$ as a theoretical capacity of 4,000 mmeq K$^+$ ions to generate 20 mM KOH at 1.0 mL/min, the device will have a useful lifetime of 2500 hours, assuming a 75 percent consumption of K$^+$ ions in its K$^+$ ion supply reservoir before replacing the salt solution.

Figure 4:
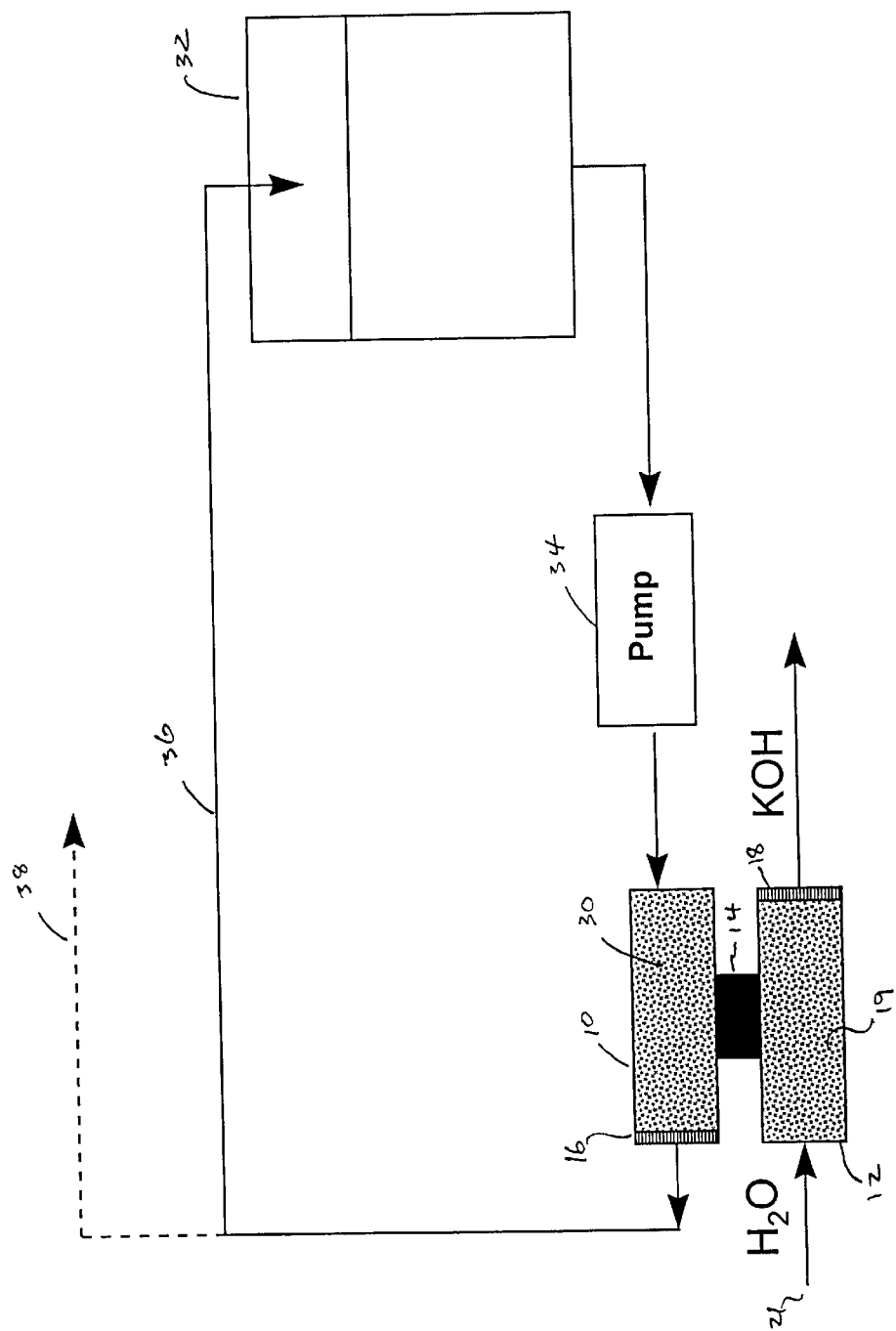

FIG. 4 illustrates a flow-through strongly acidic cation exchange resin bed 30 in K$^+$ form disposed in reservoir 10. Anode 12 is suitably in the form of a perforated platinum electrode at its outlet and adjacent an outlet port, not shown. Generation chamber 12 is separated from reservoir 10 by barrier 14 of the type described above. In this instance, cation solution in the form of the potassium salt (e.g., 2.0 M K$_2$HPO$_4$) is continuously pumped by a pump 34 to a reservoir 10 at a desired rate (e.g. about 0.1 to 2.0 mL/min). The same principles described above with respect to concentration of the potassium salt and the type of salt applied to this embodiment as well. Similarly, the same flows and reactions occur in generator 12.

Continuous pumping of the potassium salt solution leads to a continuous supply of K$^+$ ions until the solution of salt in the remote reservoir is consumed. In one embodiment illustrated in FIG. 4, the potassium salt solution is recycled in recycle line 36 from the outlet of reservoir 10 to the inlet of remote reservoir 32. The system can be operated until the concentration of K$^+$ ions in remote reservoir 32 has been decreased to a level insufficient to consistently generate KOH at the desired concentration. Then the device can be replenished by replacing the potassium salt solution in the remote reservoir 32. Alternatively, in the non-recycle mode, the solution exiting reservoir 10 flows to waste as illustrated by dotted line 38. The flow rate of the potassium salt solution can be slightly adjusted (e.g., about 0.005 to 0.050 mL/min) to provide a sufficient supply of K$^+$ ions to generate KOH at the desired concentration. Similarly, the device is replenished by filling the remote reservoir with potassium salt solution when the concentration has dropped below the desired level.

In another embodiment of the invention, not shown, ion exchange resin 30 may be eliminated from reservoir 10 so reservoir 10 is filled with salt solution flowing from a remote reservoir 32. Otherwise the system is identical to the one described above.

Figure 5:
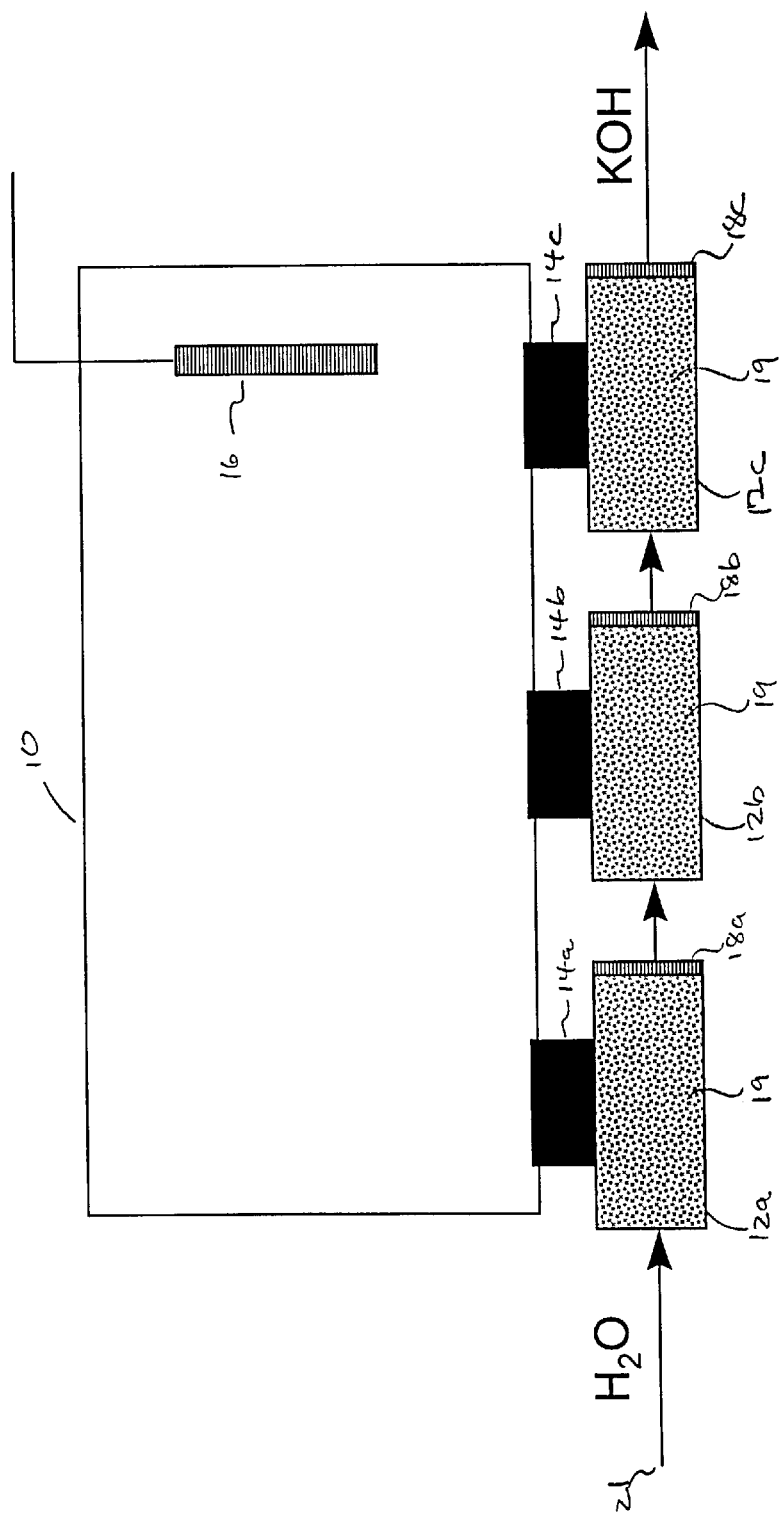

Referring to FIG. 5, another embodiment of the invention is illustrated including multiple generation chambers 12a, 12b, and 12c connected in series, each one including its own cathodes 18a, 18b, and 18c. Generation chambers 12a, 12b, and 12c are connected to reservoir 10 by barriers 14a, 14b, and 14c as described above. The difference is that there are smaller generation chambers and smaller barriers. By way of example, if each generation chamber is applied with a current of 80 mA to generate 25 mM of KOH at 2.0 mL/min the KOH generator with three generation chambers is capable of producing about 75 mM of KOH at 2.0 mL/min. Additional KOH generation chambers may also be employed. An advantage of using two or more generation chambers is that the operating voltage of the system may be lowered because the applied current used to generate KOHs distributed among the generation chambers. Thus higher currents may be applied to generate the base of higher concentrations without being limited by potentially excessive heating.

In another embodiment, not shown, two or more cathodes may be disposed in a generation chamber 12, preferably spaced along the length of the chamber in the direction of aqueous liquid flow, e.g. near the inlet and outlet. This can serve to lower the electrical resistance of the chamber and thus the operating voltage of the system.

Figure 6:
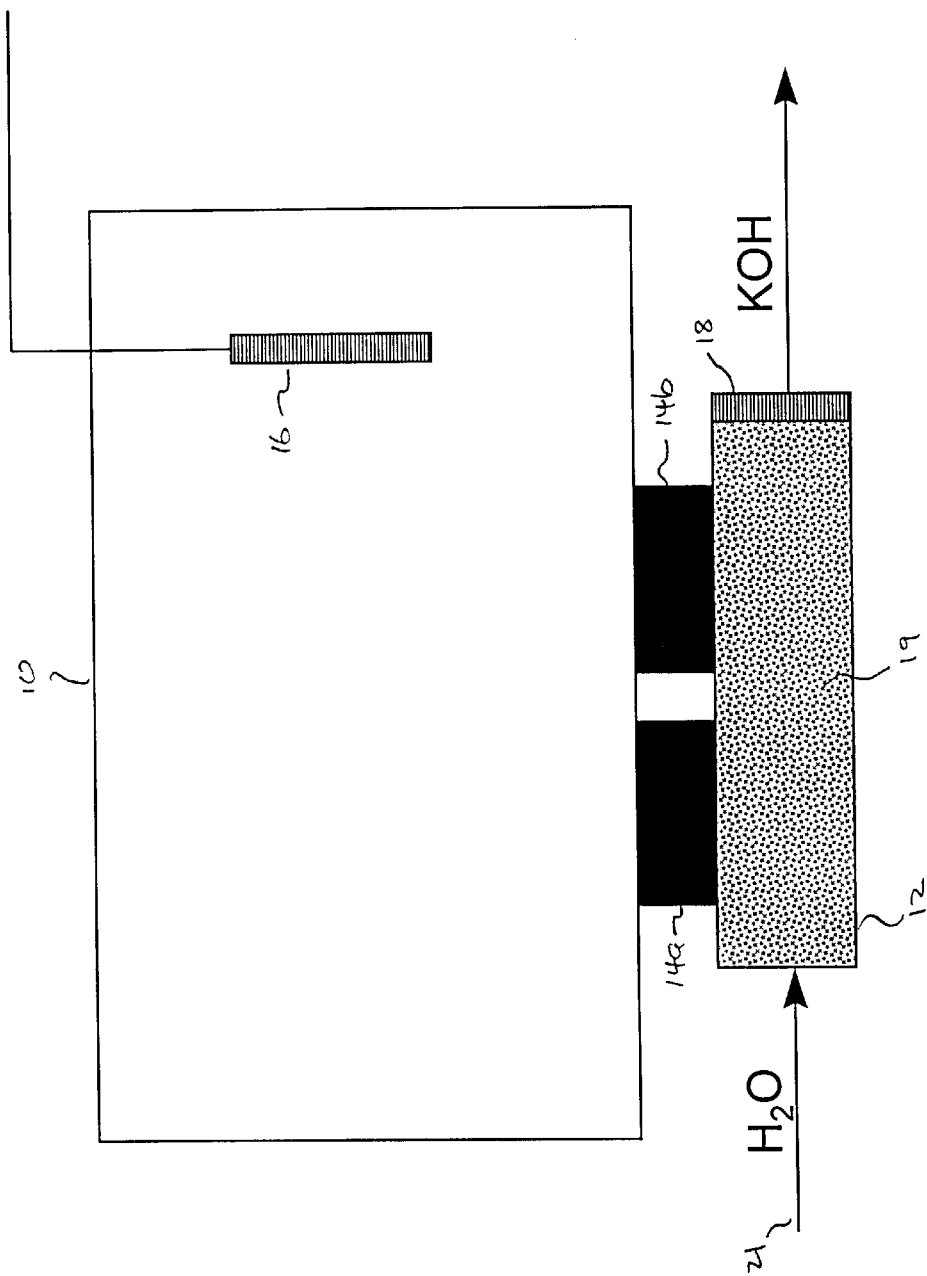

Referring to FIG. 6, another embodiment of the invention is illustrated using a single generation chamber 12 and two barriers 14a and 14b interconnecting chamber 12 and reservoir 10. Use of multiple barriers can reduce the device operating voltage. Therefore the generation chamber 12 can be supplied with higher currents to generate KOH at higher concentrations without being limited by potentially excessive heating. Another advantage in the use of multiple barriers is that flexible membranes of smaller areas have better resistance to bursting than larger area membranes.

Figure 7:
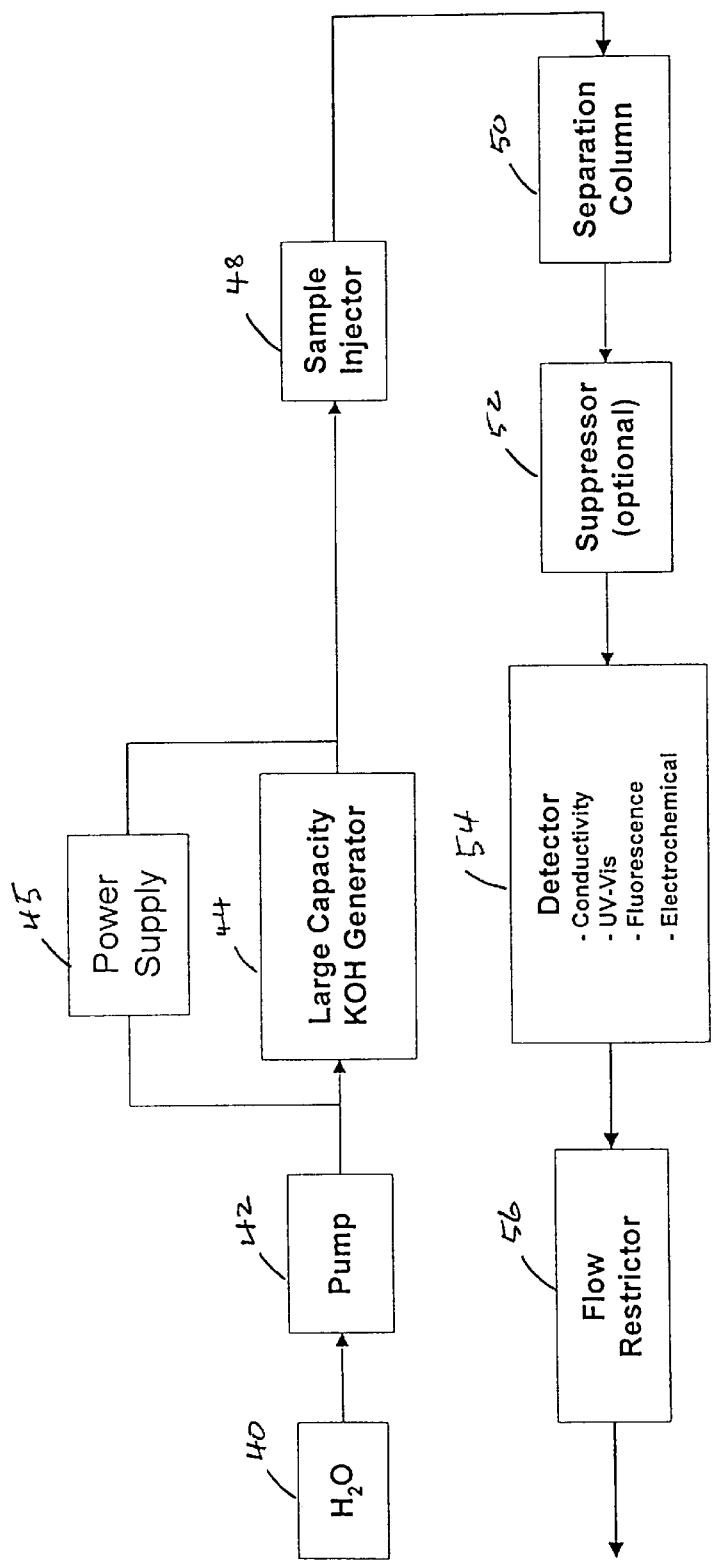

Referring to FIG. 7, use of the KOH generator of the present invention is schematically illustrated on-line in an ion chromatography or liquid chromatography system. Water from source 40 is pumped by pump 42 through the generation chamber of the large capacity KOH generator 44 with an anode in the cation source reservoir and a cathode in the generation chamber connected to a power supply 45, as described above. Generator 44 is on-line with a conventional simplified ion chromatography system. Pump 42 is a conventional chromatography pump which pumps the KOH output from generator 44 through sample injection valve 48 into chromatographic separator 50 packed with a chromatographic separation medium, typically an ion exchange resin packed bed column. Alternatively, other forms of separation medium may be used such as porous hydrophobic chromatographic resin with essentially no permanently attached ion exchange sites.

In ion chromatography, the effluent from the separation column 50 flows through suppressor 52 serving to suppress the conductivity of the base and the effluent from separator 50, but not the conductivity of the ions injected through sample injector 48. Then, the effluent from suppressor 52 is directed through a flow through detector 54, e.g. a conductivity detector, for detecting the resolved ions in the effluent from suppressor 52. A suitable data system, not shown as provided in the form of a conventional conductivity detector for measuring the suppressor effluent in the conductivity cell in which the presence of an ionic species produces an electrical signal proportional to its concentration. With the exception of generator 44, such ion chromatography systems are well known as illustrated in U.S. Pat. Nos. 3,897,213; 3,920,397; 3,925,019; and 3,956,559 incorporated herein by reference.

Other forms of detectors 54 may also be employed and the suppressor may be eliminated. Such other forms of detection include UV, fluorescence and electrochemical.

In the large capacity KOH generator, electrolysis reactions produce hydrogen and oxygen gases. When used in a chromatography system, the hydrogen gas, along with the KOH solution, is carried forward into the chromatographic flow path. If hydrogen gas is produced in a significant volume relative to the liquid flow, its presence can be detrimental to the downstream chromatography process. The potential problem of hydrogen gas can be eliminated by application of Boyle's law. A flow restrictor can be placed after the detector flow cell to elevate the pressure of the entire chromatography system. Under high pressure (e.g., 1000 psi or higher pressures), hydrogen gas is compressed to an insignificant volume compared to the eluent flow so that it does not interfere with the downstream chromatography process. This approach requires the use of a detector flow cell capable of withstanding a pressure of 1000 psi or more. In an ion chromatography system using suppressed conductivity detection, the above approach also requires the use of a suppressor that is capable of withstanding a pressure of 1000 psi or more. The necessary pressure to accomplish this depends on the volume of gasses produced. However, for a typical system, a pressure of at least 250 to 500 psi is sufficient. One mode of elevating the pressure is to connect a flow restrictor 56 such as a fine bore coiled tubing downstream of the detector (e.g. three meters of 0.005 in I.D.). This elevates the pressure throughout the chromatography system upstream of the detector.

Figure 8:
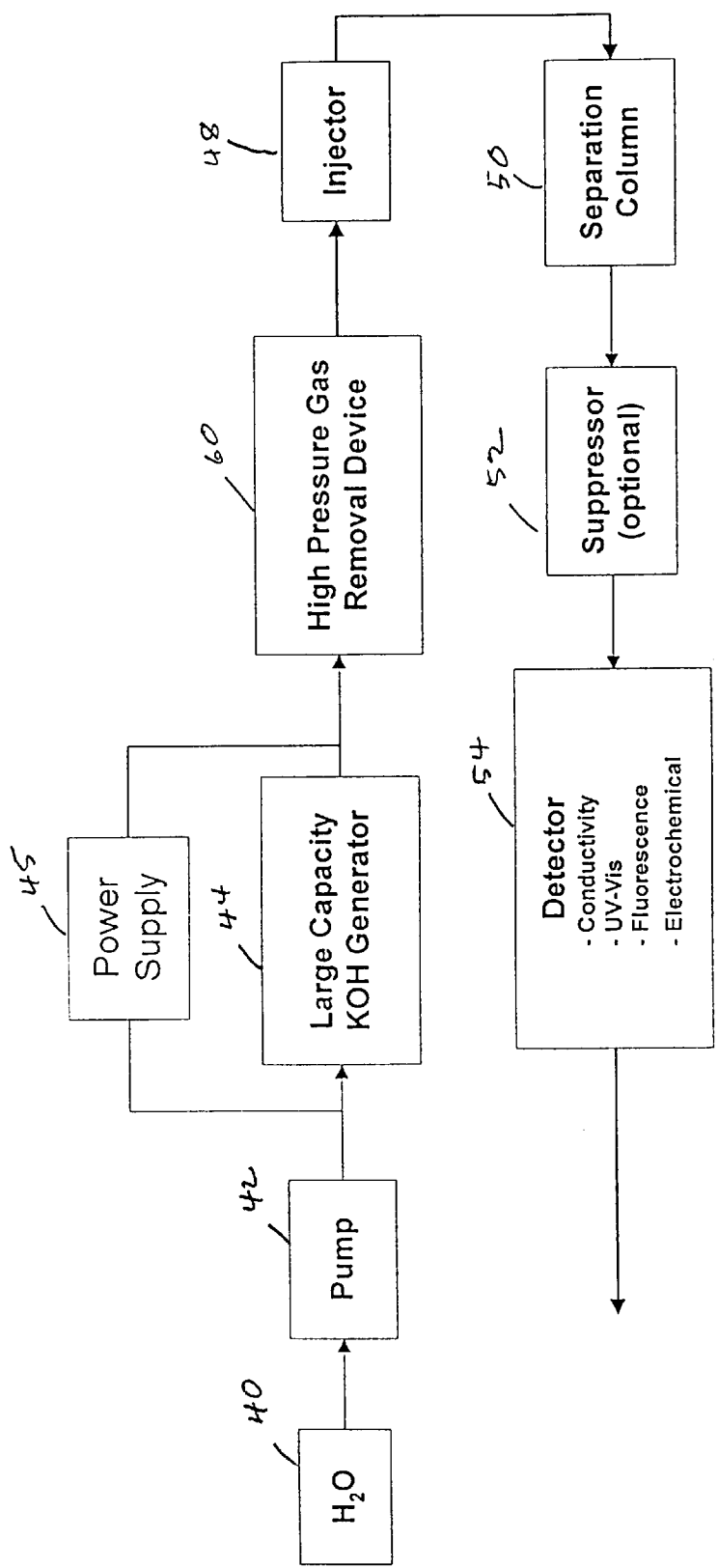

Another approach to eliminate the potential problem associated with hydrogen gas is to use an on-line pressure gas removal device to remove hydrogen gas from the KOH solution. FIG. 8 illustrates a schematic outline of an ion chromatography system employing a large capacity KOH generator and an on-line high pressure gas removal device 60 instead of flow restrictor 56 in FIG. 7. In this implementation, a high pressure gas removal device 60 is placed downstream of the outlet of the large capacity KOH generator 44, suitably between it and sample injector 48. Hydrogen gas is effectively removed from the KOH eluent before it reaches the sample injector of the chromatography system so that the downstream chromatographic process is not affected. One advantage of this system is that a conventional detector flow cell and ion chromatography suppressor can be used.

Figure 9:
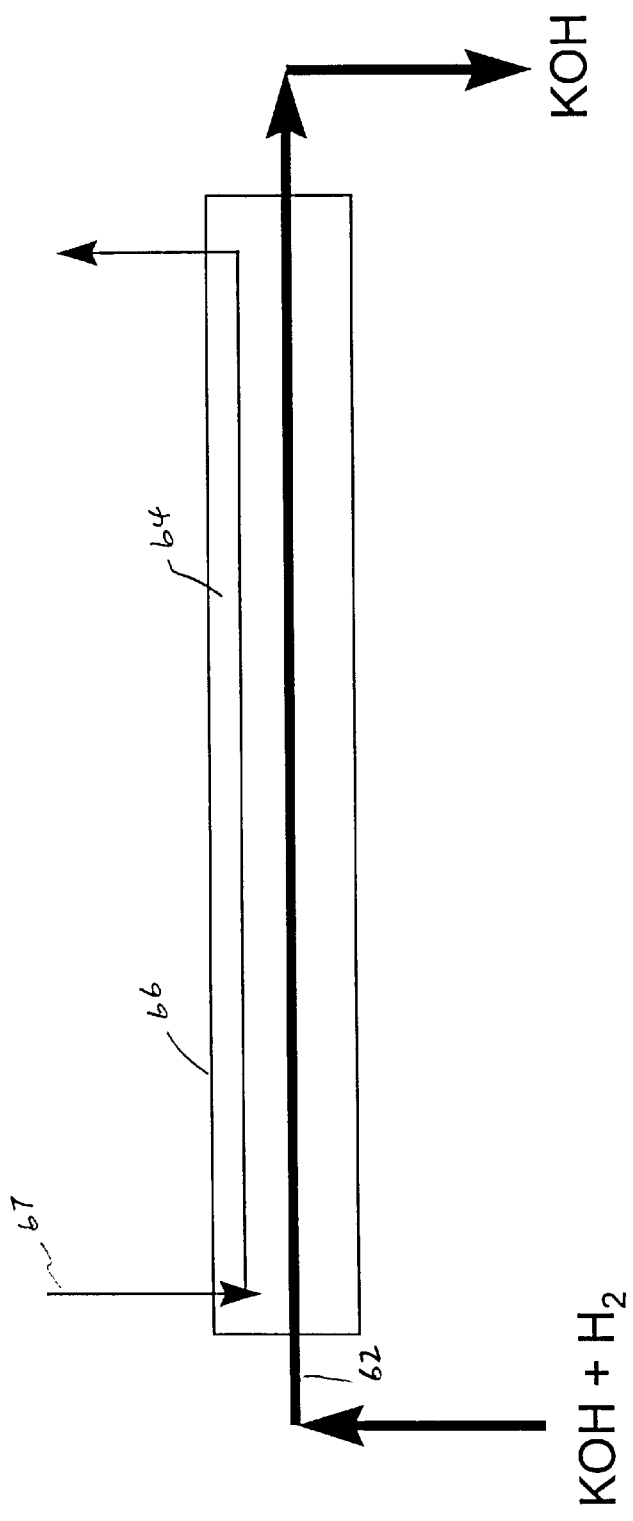
FIG. 9 is an on-line high pressure gas removal device for use in the present invention.

One preferred embodiment of the on-line high pressure gas removal device is shown in FIG. 9. In this embodiment, gas permeable polymeric tubing 62 is used to remove hydrogen gas in the KOH product solution under high pressure. Aqueous solution 67 flows in an annular space 64 outside of the gas permeable tubing 62 defined between tubing 64 and protective tubing 66. The released hydrogen gas is removed from the device by in the flowing aqueous liquid stream in space 64 which also serves to prevent absorption of carbon dioxide from the ambient air into the KOH product stream. One source of the aqueous liquid in space 64 is the detector effluent.

Preferably, the polymeric tubing 62 is inert and has high burst pressure and high gas permeability. The inner volume of the gas permeable tubing should be small so that it does not have large dead volume and thus does not compromise the gradient performance of the large capacity eluent generator. It is preferred to use a gas permeable tubing with inside diameter less than 0.015 inch so that the gas removal device has low dead volume and high burst pressure.

The polymeric tubing prepared from a number of polymers including polymethylpentene, polypropylene, and fluoropolymers such as PTFE, ETFE, PFA, and FEP is gas permeable under high pressure and may be used as the gas removal tubing for the eluent generator.

The on-line high pressure gas removal device shown in FIG. 8 can also be used to remove oxygen gas generated along with the acid solution in a large capacity acid generator.

In another embodiment of the invention, not shown, the system of FIG. 7 can be used in gradient ion or liquid chromatography where eluent components in addition to KOH are required. A gradient pump, e.g. a Dionex GP-40 pump type, can be used to deliver a prescribed mixture of one or more eluent components from separate reservoirs to the high pressure KOH generation column. The eluent is modified with KOH which is generated on-line at the exit end of the KOH generation column. The concentration of KOH in the final eluent delivered to the separation column can be controlled by controlling the applied current to the large capacity KOH generator. The gradient system using the large capacity KOH generator is especially beneficial to applications that require the use of highly pure base hydroxide solution.

Figure 10:
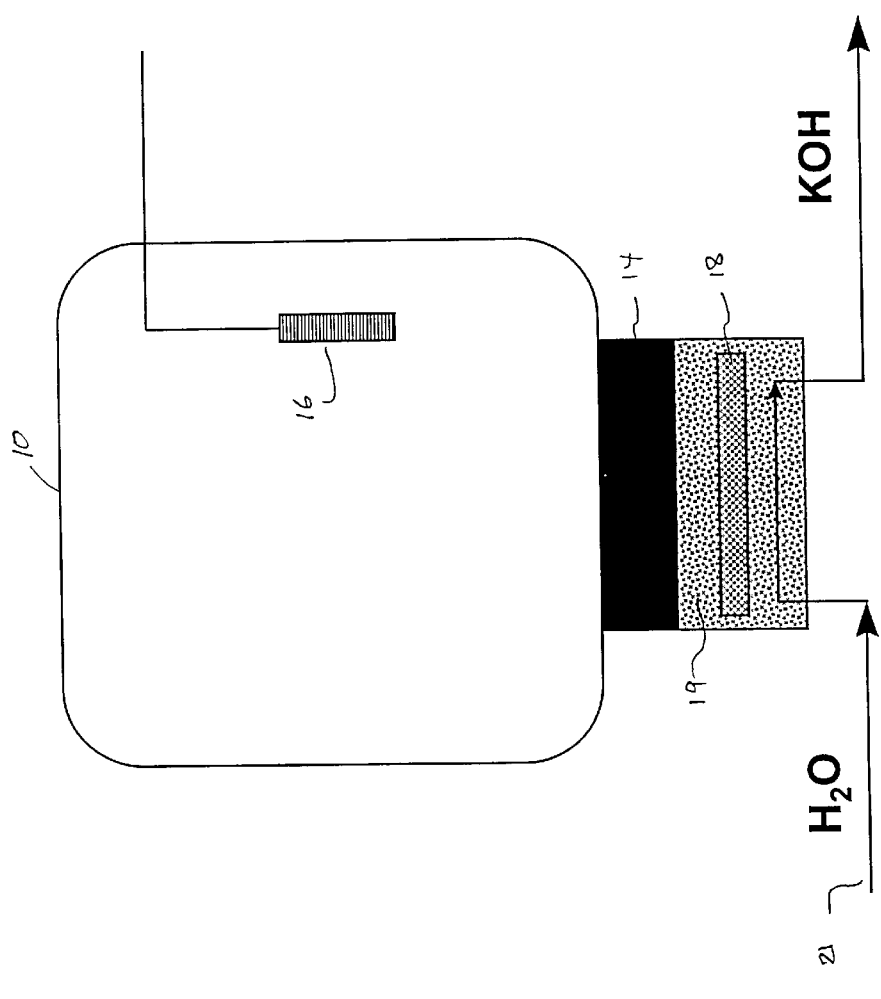

Referring to FIG. 10, another form of the present invention is illustrated. Here reservoir 10 includes a solution of cation salt solution (e.g. one liter of $K_2HPO_4$ at 2 M concentration). Barrier 14 extends substantially along the entire length of the mating side generation chamber 16 in open communication with the interior of the chamber. Cathode 18 is in the form of a perforated platinum cathode which extends along the flow path of the aqueous stream through chamber 12 in direct contact with beds of ion exchange resin 19 in $K^+$ form on both sides of cathode 18. Water flows through an inlet port, not shown, on the upstream side of the chamber. The KOH produced in chamber 12 exits at an outlet port, not shown, at the downstream side of the chamber. The perforated platinum cathode is in the form of a screen suitably extending along the entire length of resin bed and is perforated to permit passage of solution through the cathode to ensure an efficient removal of KOH generated.

Figure 11:
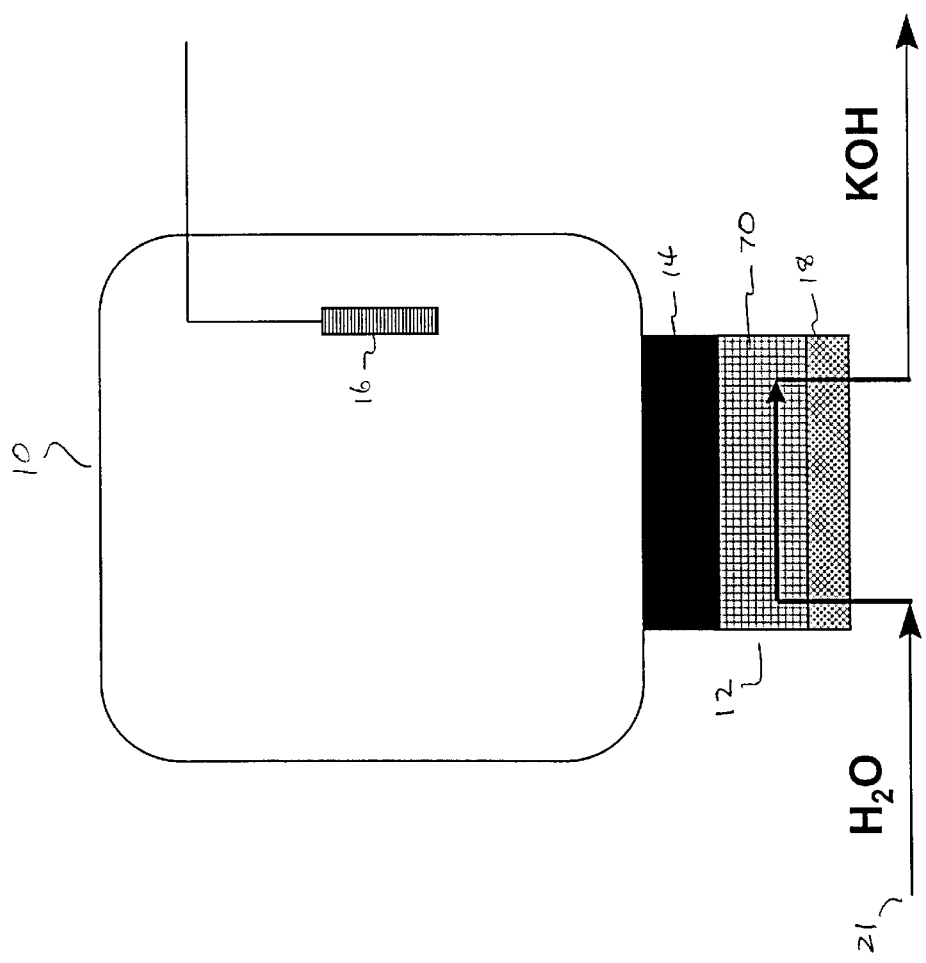

Another form of generation chamber 12 is illustrated in FIG. 11. This embodiment differs from that of FIG. 9 in the use of a cation exchange screen 70 in contact with perforated cathode 18 on one side and with barrier 14 on the other side. The electrical path between anode 16 and cathode 18 extends through barrier 14, cation exchange screen 10 and perforated cathode 18. The aqueous stream flows through the chamber 12 inlet port, through perforated cathode 18 into cation exchange screen 70 where it flows adjacent to the cathode and out the chamber 12 outlet on the downstream side of screen 70.

In another embodiment of the generation chamber, not shown, the only structural eluent within chamber 12 is cathode 18 in the form of a perforated platinum electrode screen in direct contact with barrier 14. The aqueous stream flows through the perforated platinum cathode screen. The screen uses openings of a size suitably on the order of 50–100 $\mu$m to permit the flow of the aqueous stream through the platinum screen without undue pressure drops. A suitable screen has a size of 1 to 5 $cm^2$.

Figure 12:
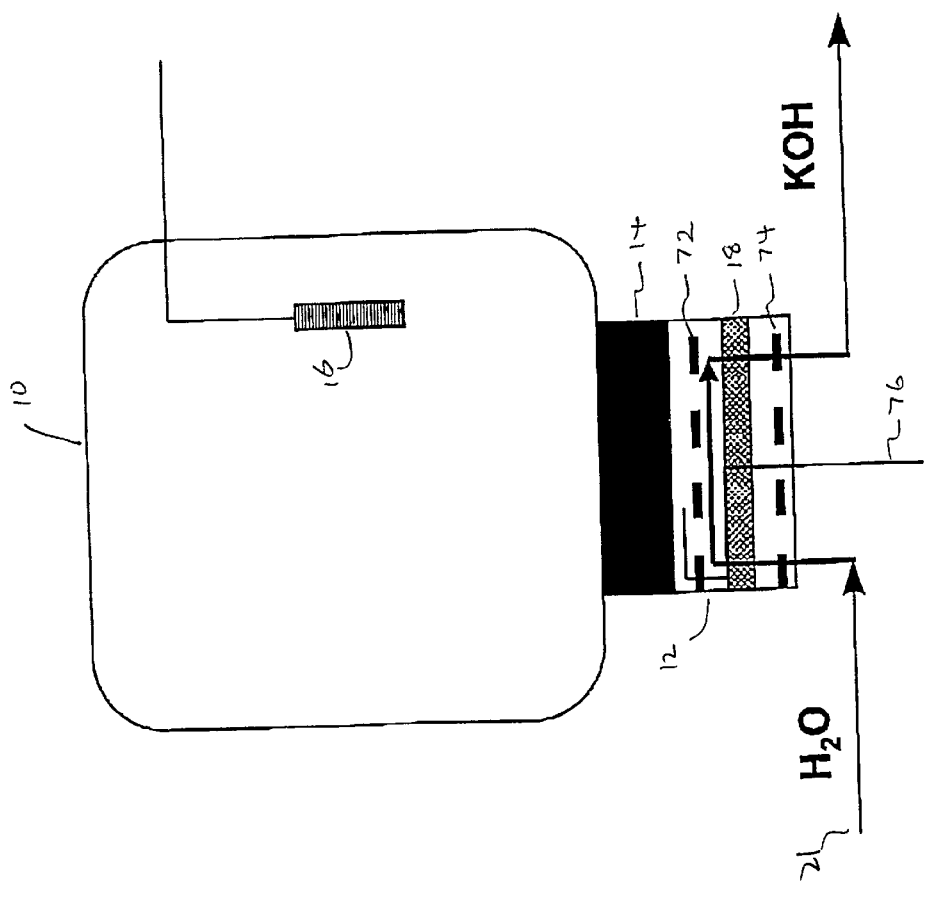

Another embodiment of the base generation chamber design is illustrated in FIG. 12. As in the embodiment of FIG. 10, barrier 14 extends along the entire length of chamber 12. In this instance, the perforated platinum cathode 18 is sandwiched between non-charged screens 72 and 74 suitably formed of a non-charged polymer such as a polypropylene which forms the fluid pathway in the generation chamber 12. Screens 72 and 74 may be of the same size as the screen cathode in the embodiment of FIG. 11. An inert lead, e.g. platinum wire 76, provides electrical contact with platinum cathode 18 and in direct contact with barrier 14. Upon the application of electrical current a small amount of KOH is formed in situ. The KOH serves as the ion transport bridge between barrier 12 and platinum electrode 18. Screens 72 and 74 have sufficient porosity to permit the flow of water through the screen without undue pressure drop.

The system of FIG. 12 can be operated by first filling chamber 12 with KOH solution prepared externally which serves as the ion transport bridge between barrier 14 and cathode 18. Then current is applied. Good contact between the perforated disk-cathode 18 and barrier 14 may be maintained by pressing one against the other. The electrode can extend across all or part of the aqueous liquid flow path through the chamber 12 to permit intimate contact with the flowing aqueous stream.

Other embodiments of the interior configuration of the base generation chamber may be employed so long as there is sufficient electrical path between the anode and the cathode to permit the cations to transport across the barrier and with the aqueous stream flowing through the chamber to permit the efficient generation of KOH. It has been found that systems in which the cathode and a barrier in the form of a charged membrane extends substantially along the entire flow path of the aqueous stream through the base generation chamber is very efficient.

The system has been described with respect to generating a base and specifically KOH. However, the system is also applicable to the generation of an acid by reversal of the polarity of the ion exchange beds, barrier and the electrodes. In this instance, anion exchange beds, rather than cation exchange beds are employed. Also the barriers are of a type which pass anions but not cations and block the flow of liquid. Suitable barriers for use in the production of acid can be prepared from a single or multiple ion exchange membrane of appropriate thickness or a block or rod of ion exchange material. A suitable form of membrane is supplied by Membrane International of Glen Rock, N.J. (designated AMI-7000 anion exchange membrane).

The cations or anions for use as the source in reservoir 10 must also be sufficiently water soluble in base or acid form to be used at the desired concentrations. Suitable cations are metals, preferably alkali metals such as sodium, potassium, lithium and cesium. Known packing for high capacity ion exchange resin beds provide such cations or anion for use in the embodiment where resin is used as the source of cations or anions. Typically, the resin support particles would be in the potassium or sodium form. Potassium is a particularly effective exchangeable cation because of its high conductance. Suitable other cations are tetramethyl ammonium and tetraethyl ammonium. Analogously, suitable exchangeable anions for cation analysis include chloride, sulfate and methane sulfonate.

Using the concept described above, a large capacity acid generator can also be implemented. For example, a large capacity methanesulfonic acid (MSA) generator employing a $CH_3SO_3^-$ ion supply reservoir is described here as an example. MSA generation chamber 12 is packed with a strongly basic anion exchange resin in $CH_3SO_3^-$ form and equipped with a Pt screen electrode (anode) which is in direct contact with the anion exchange resin. The MSA generation chamber 12 is connected to the $CH_3SO_3^-$ ion supply reservoir 10 using one or more anion ion exchange barriers of the same general type as barrier 14. Barrier 14 permits the passage of $CH_3SO_3^-$ ions from the supply reservoir into the resin bed in the MSA generation column, while precluding the passage of cations from the $CH_3SO_3^-$ ion supply reservoir into the MSA generation column. Barrier 14 also serves the role of a high pressure physical barrier that insulates the low pressure $CH_3SO_3^-$ ion supply compartment from the high pressure MSA generation chamber 12.

Analogous to the cation-source reservoir, the anion-source ($CH_3SO_3^-$) reservoir 10 is equipped with a cathode and a gas vent hole. The reservoir (1 to 2 liters in volume) is filled with a solution of a MSA salt such as $NH_4CH_3SO_3$. The concentration of $CH_3SO_3^-$ ions in the solution is preferably 1 to 2 M or higher so that there is a sufficient amount of $CH_3SO_3^-$ ions in the $CH_3SO_3^-$ ion supply reservoir for the generation of MSA over an extended period of time; however, the MSA salt solution containing $CH_3SO_3^-$ ions at lower concentrations can be used. It is preferred that the cation of the MSA salt used can not be reduced by the cathode int he $CH_3SO_3^-$ ion supply reservoir. It is also preferred to use a "weakly basic cation" (e.g., $NH_4^+$) defined to have a base dissociation constant ($pK_b$) of 4.5 or higher so that the concentration of free $OH^-$ ions in the solution is kept lower than 0.1 mM. A "strongly basic cation" is defined to have a base dissociation constant ($pK_b$) of less than 4.5. $OH^-$ ions, like $CH_3SO_3^-$ ions, can migrate across the anion exchange connector into the MSA generation column. If $OH^-$ ions migrate across the anion exchange connector into the MSA generation column in significant amounts, the direct linear relationship between the applied current and the concentration of MSA generated is lost because $OH^-$ ions can combine with $H^+$ ions generated at the anode to form water, and thus the performance of the MSA generator is compromised.

To operate the large capacity MSA system, deionized water is pumped through the MSA generation chamber 12, and a DC voltage is applied between the anode is and cathode 18. Under the applied field, the electrolysis of water occurs at the anode and cathode. Water is reduced to form $OH^-$ ions and hydrogen at the cathode:

$$2H_2O+2e^- \rightarrow 2OH^-+H_2\uparrow \qquad (4)$$

and oxidized to form $H^+$ ions and oxygen at the anode:

$$H_2O+2e^- \rightarrow 2H^++1/2O_2\uparrow \qquad (5)$$

$CH_3SO_3^-$ ions migrate through barrier 14 into the resin bed in the MSA generation chamber 12, and eventually combine with $H^+$ ions generated at the anode to produce a MSA solution suitable for use as a high purity eluent for ion or liquid chromatography.

The large capacity acid or base generator can also be implemented to generate high purity ion pairing reagents such as octanesulfonic acid (OSA) and tetrabutylammonium hydroxide (TBAOH) for use as eluents in mobile phase ion chromatography (MPIC) or reversed-phase ion pair chromatography (RPIPC).

Although much of the above discussion relates to use of the generated base or acid in ion and liquid chromatography, such use can also be applied to other areas such as titration, flow injection analysis and post-column reactors.

Specifically the generated base can be used in combination with (a) conventional titration analyses, e.g. described in Douglas A. Skoog and Donald M. West, Fundamentals of Analytical Chemistry, 4th Edition, Saunders College Publishing, San Francisco, 1982, Chapter 8 Theory of Neutralization, p. 195 or Douglas A. Skoog, Principles of Instrumental Analysis, 3rd Edition, Saunders College Publishing, San Francisco, 1985, Chapter 20 Potentiometric Methods, p. 638; (b) flow injection analysis, e.g., described in Theory and Automation, Skoog, Chapter 29, p. 858–859; and (c) post-column reactors, e.g. described in Paul R. Haddad and Peter E. Jackson, Ion Chromatography, Elsevier, N.Y., 1988, p. 387 and R. W. Frei Editor and K. Zech, Selective Sample Handling and Detection in High-Performance Liquid Chromatography, Elsevier, N.Y., 1988, p. 396.

The following examples are provided in order to further illustrate the present invention.

EXAMPLE 1

Generation of KOH using a KOH generator employing a large capacity $K^+$ ion supply reservoir (as illustrated in FIG. 2).

Figure 13:
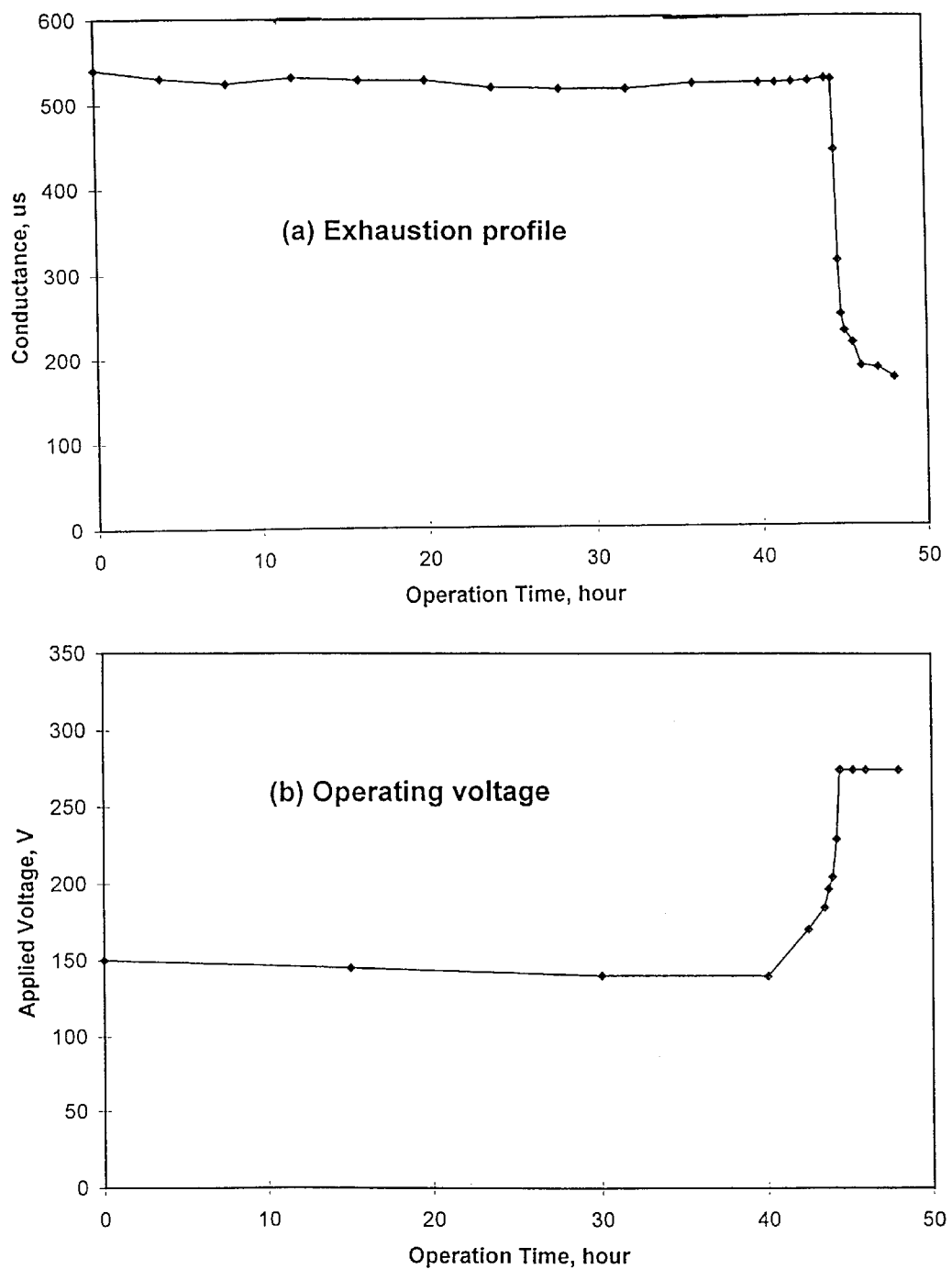
FIGS. 13–29 are graphical representations of experimental results using the present base or acid generator system.

A large capacity KOH generator consisting of a $K^+$ ion supply reservoir 10 in the form of column (18-mm ID–185-mm length) and a KOH generation chamber in the form of column 12 (4-mm ID×30-mm length) was constructed. The KOH generation chamber was packed with an 18-μm, 8% cross-link sulfonated styrene/divinyl benzene resin in $K^+$ form. The $K^+$ ion supply column consisted of a 175 mm length bed of an 18 μm, 8% cross-link sulfonated styrene/divinyl benzene resin in $K^+$ form and a 10 mm length bed of a 50 μm polyacrylate resin in $K^+$ form. The device was tested under an applied current of 30 mA and a carrier flow rate of 1.0 mL/min for 48 hours. The conductance of the KOH solution generated and the operating voltage of the KOH generator were monitored over the testing period. The exhaustion profile (the conductance of the KOH solution generated vs. time) and the operating voltage data are shown on FIG. 13. The device produced a constant output of KOH(18.7 mM KOH at the carrier flow rate of 1.0 mL/min) for 44.4 hours, or a useful capacity of 49.7 meq. After 44.4 hours of operation, the operating voltage increased to 275 V (the operating voltage limit of the power supply used in the experiment) due to the development of a less conductive neutralized zone in the weakly acidic carboxylated resin bed inside the $K^+$ ion supply column, and decreases in the operating current and concentration of KOH generated were observed. These results indicate the feasibility of using the large capacity KOH generator employing the large $K^+$ ion supply column to generate the KOH solution over an extended period of time.

EXAMPLE 2

Generation of KOH using a large capacity KOH generator employing a flow-through $K^+$ ions supply column (as illustrated in FIG. 4).

Figure 14:
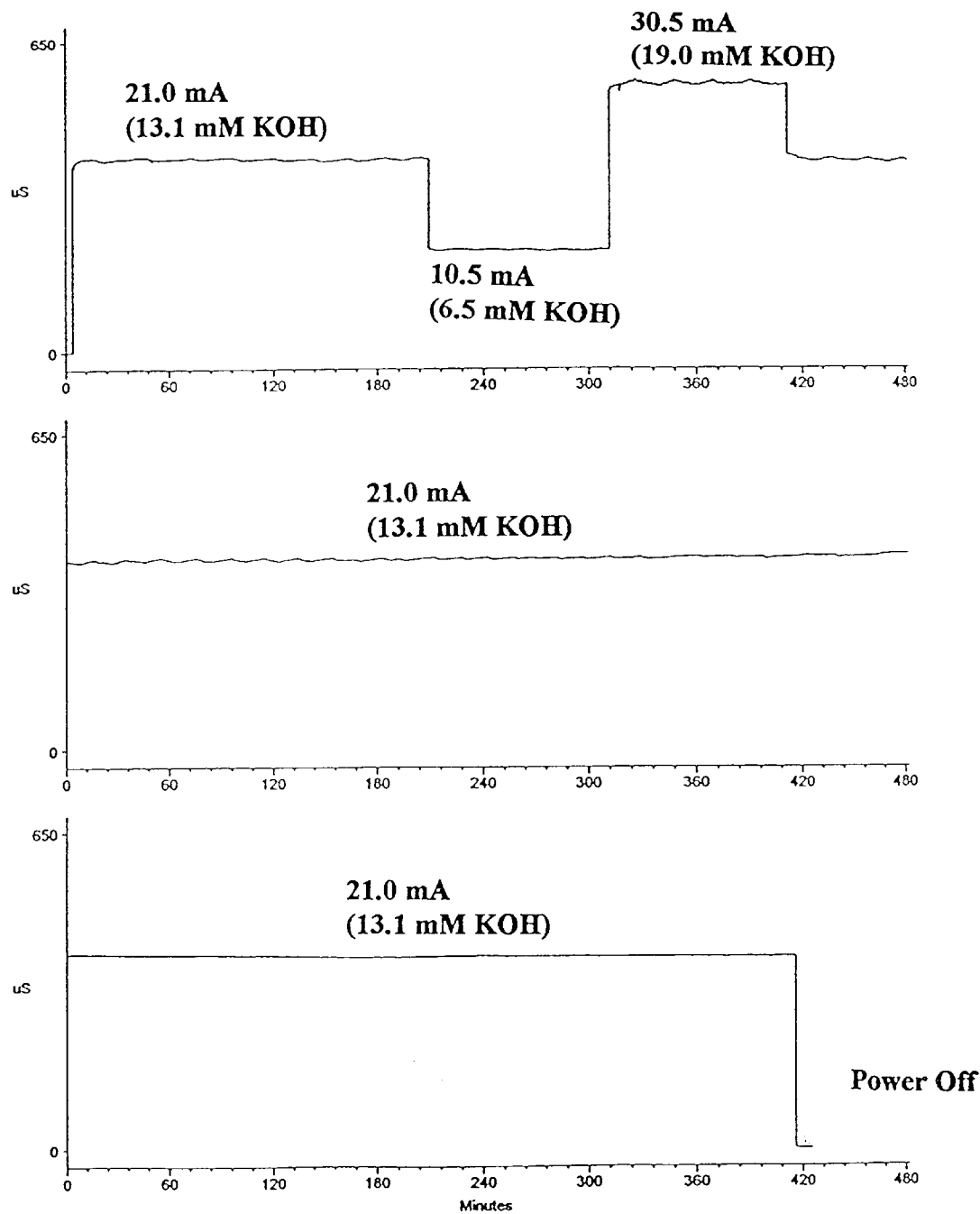

A large capacity KOH generator employing the flow-through $K^+$ ion supply column was constructed to evaluate this embodiment of the invention (FIG. 4). Both the flow-through $K^+$ ion source reservoir 10 in the form of column (4-mm ID×25-mm length) and the KOH generation chamber (4-mm ID×25-mm length) were packed with an 18 μm, 8% cross-link sulfonated styrene/divinyl benzene resin in $K^+$ form and equipped with porous Pt frit electrodes at their outlets. A 100-mM KCl solution in a remote reservoir was pumped continuously through the flow-through $K^+$ ion supply column at a flow rate of 1.0 mL/min. The large capacity KOH generator was tested under applied currents of 10.5, 21, and 30.5 mA for about 23 hours. The operating voltage ranged from 40 to 60 V during the experiment. FIG. 14 shows the conductance profiles of the KOH solutions generated at a carrier flow rate of 1.0 mL/min and applied currents of 10.5, 21, and 30.5 mA. The concentration of KOH generated was directly proportional to the applied current. The results indicate that it is feasible to use a large capacity KOH generator employing a flow-through $K^+$ ion supply column to generate the KOH solution over an extended period of time.

EXAMPLE 3

Generation of KOH using a large capacity generator employing a $K^+$ ion supply reservoir (as illustrated in FIG. 3).

Figure 15:
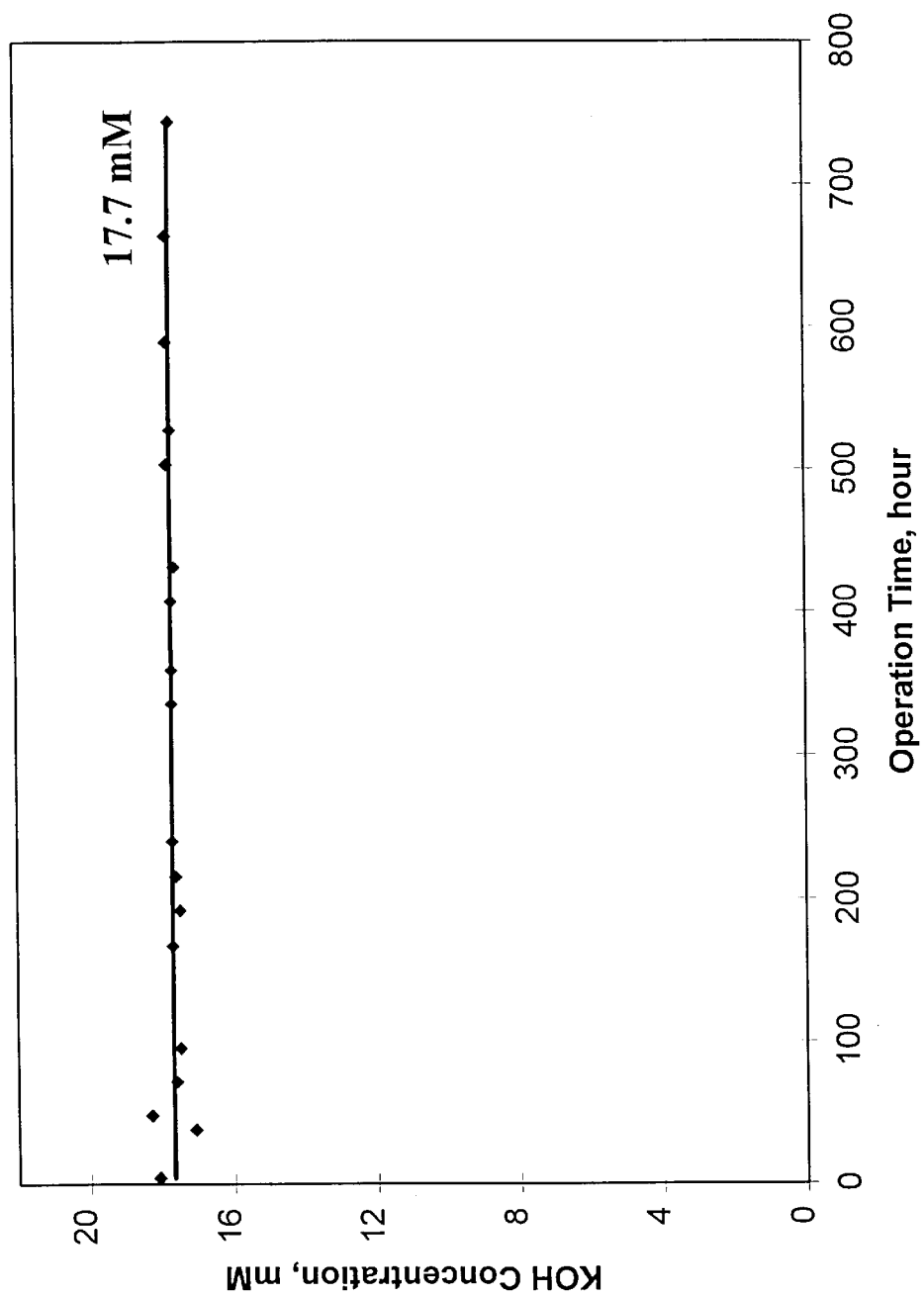

A large capacity KOH generator employing a $K^+$ ion source reservoir 10 was constructed to evaluate this preferred embodiment of the invention (FIG. 3). The KOH generation chamber (5.2-mm ID×37-mm length) was packed with an 18-μm, 8% cross-link sulfonated styrene/divinyl benzene resin in $K^+$ form and equipped with a porous Pt frit electrode at its outlet. The $K^+$ ion source reservoir 10 was filled with a 2.0 M $K_2HPO_4$ solution. The large capacity KOH generator was operated continuously under a constant current of 30 mA and a carrier flow rate of 1.0 mL/min for a total of 832 hours. The operating voltage was about 60 V during the test. The KOH solutions generated using the device were periodically collected and titrated using a 10-mM nitric acid standard to determine the concentration of KOH generated. FIG. 15 shows the determined concentration of KOH in the solutions collected. Over the period of 744 hours, the average determined KOH concentration was 17.7 mM (n=18 and RSD=2.2%), corresponding to 95% of the theoretical concentration of 18.7 mM. The results indicate that it is feasible to use a large capacity KOH generator employing a large capacity $K^+$ ion supply reservoir to generate the KOH solution over an extended period of time.

EXAMPLE 4

Generation of KOH using a large capacity generator employing a $K^+$ ion supply reservoir and three KOH generation chambers (as illustrated in FIG. 5).

A large capacity KOH generator employing a $K^+$ ion supply reservoir and three KOH generation chambers, as illustrated in FIG. 5, was constructed. Each KOH generation chamber (5.2-mm ID×10-mm length) was packed with an 18-μm, 8% cross-link sulfonated styrene/divinyl benzene resin in $K^+$ form and equipped with a porous Pt frit electrode at its outlet. The $K^+$ ion supply reservoir was filled with a 2.0 M $K_2HPO_4$ solution. The large capacity KOH generator was used to generate KOH solutions under applied currents ranging from 10 to 160 mA and carrier flow rates of 1.0 or 2.0 mL/min. The operating voltage for the KOH generator was 45 V when an applied current of 160 mA was maintained to generate 50 mM KOH at 2.0 mL/minute.

Figure 16:
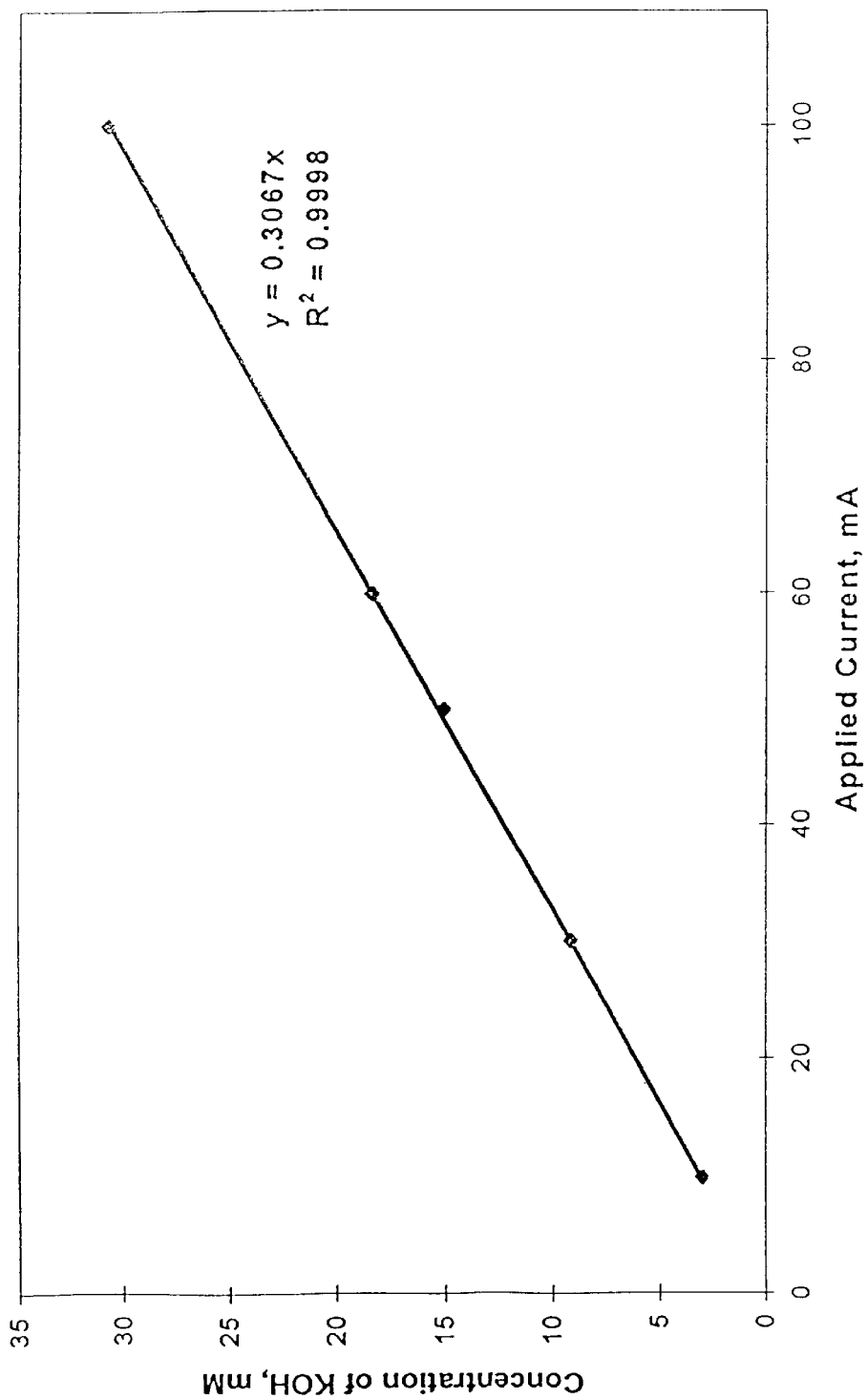

The concentrations of KOH generated at different applied currents using the KOH generator were determined by titration using a 10-mM nitric acid standard. The results are summarized in Table 1. In this KOH generator, the KOH solution generated in the first KOH generation chamber flows through the second and third KOH generation chambers. The presence of KOH solution in the second and third KOH generation chambers did not affect the KOH generation in the second and third chamber. The percent electrolytic yield of this KOH generator was very close to the theoretical limit, ranging from 96.8 percent at 10 mA to 99.0 percent at 100 mA, as shown in Table 1. There was also excellent correlation ($R^2$=0.9998) between the applied current and the determined concentration of KOH generated (FIG. 16).

TABLE 1

Calculated and Determined Concentrations of KOH Generated Using a Large Capacity KOH Generator with Three KOH Generation Chambers

| Applied Current | Flow rate, mL/min | Calculated Concentration, mM | Determined Concentration[a] mM (n = 3) | Percent Yield[b] (n= 3) | Percent RSD (n= 3) |
|---|---|---|---|---|---|
| 10 mA | 2.0 | 3.1 | 3.0 | 96.8 | 0.2 |
| 50 mA | 2.0 | 15.5 | 15.1 | 97.4 | 0.4 |
| 100 mA | 2.0 | 31.1 | 30.8 | 99.0 | 0.9 |
| 100 mA | 1.0 | 62.2 | 61.2 | 98.4 | 0.5 |
| 30 mA + 10 mM NaOH | 2.0 | 19.3 | 19.2 | 98.9 | 0.9 |
| 60 mA + 10 mM NaOH | 2.0 | 28.7 | 28.4 | 98.4 | 1.3 |

[a] The number of determinations was three.
[b] Percent yield was calculated using the following definition: Percent yield = (Determined concentration − Calculated concentration)/Calculated concentration *100

The above results indicate that connecting multiple KOH generation chambers in series is a viable approach to boost the concentration of KOH generated. The results also demonstrate that KOH at relatively high concentrations can be accurately generated using a large capacity KOH generator with multiple KOH generation chambers without being limited by excessive heating.

EXAMPLE 5

Evaluation of a large capacity KOH generator employing a KOH generation chamber with multiple ion exchange connectors (as illustrated in FIG. 6).

A large capacity KOH generator employing a $K^+$ ion source reservoir and a KOH generation chamber in the form of column with two multiple ion exchange connectors, as illustrated in FIG. 7, was constructed. The $K^+$ ion supply reservoir was filled with a 2.0 M $K_2HPO_4$ solution. The KOH generation chamber 12 in the form of column ((5.2-mm ID)×10-mm length) was packed with an 18-$\mu$m, 8% cross-link sulfonated styrene/divinyl benzene resin in $K^+$ form and equipped with a porous Pt frit electrode at its outlet. The KOH generation column was connected to the $K^+$ ion supply reservoir using either one or two ion exchange connectors (each with a 5 mm in contact diameter) during the experiment. The applied current was varied from 10 to 90 mA and the operating voltage was monitored. The carrier flow rate was maintained at 2.0 mL/minute.

Figure 17:
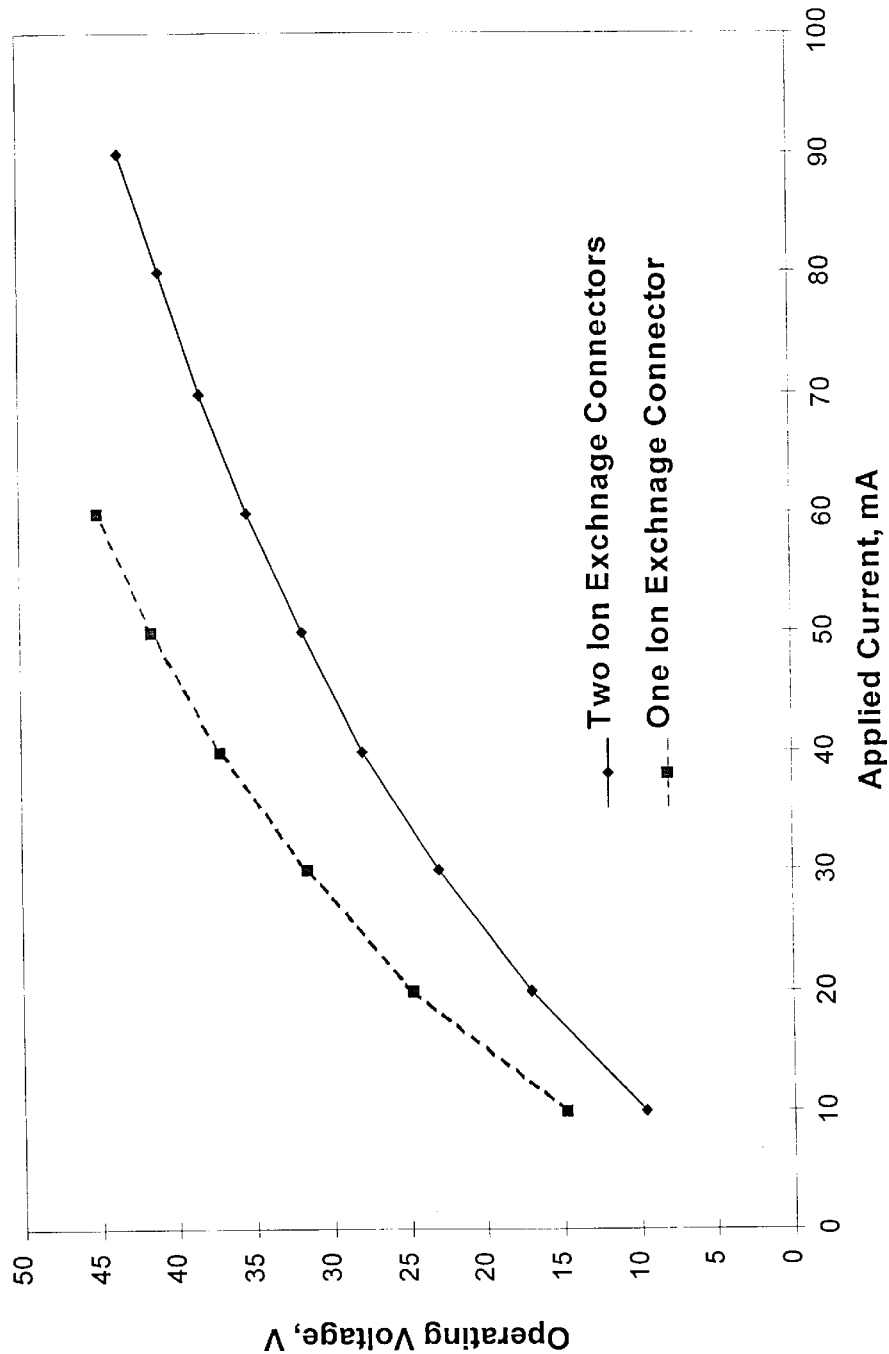

The dependence of the operating voltage on the applied current determined for the KOH generator is shown in FIG. 17. For a given applied current, the operating voltages required for the generator using two ion exchange connectors were about 30 percent lower than those required for the generator using one ion exchange connector. The use of multiple ion exchange connectors in a single KOH generation column clearly increases the pathway for the transport of $K^+$ ions from the $K^+$ ion supply reservoir into the KOH generation column and thus reduces the device operating voltage. The results suggest that the use of multiple ion exchange connectors in a single KOH generation column is a viable approach to facilitate the generation of KOH at relatively high concentrations.

EXAMPLE 6

Evaluation of different cathode configurations for the large capacity KOH generator.

A large capacity KOH generator employing a $K^+$ ion source reservoir, as illustrated in FIG. 3, was constructed. The $K^+$ ion supply reservoir was filled with a 2.0 M $K_2HPO_4$ solution. The KOH generation chamber in the form of column (5.2-mm ID×10-mm length) was packed with an 18 $\mu$m, 8% cross-link sulfonated styrene/divinyl benzene resin in $K^+$ form. The KOH generation column was connected to the $K^+$ ion supply reservoir using one ion exchange connector (5 mm in contact diameter). Three cathode configurations were tested for the KOH generation column: one porous Pt frit (4 mm diameter) placed at the outlet of the generation column, two porous Pt frits (4 mm diameter) placed at the inlet and outlet of the generation column, and a Pt screen that is formed to wrap around the resin bed in the KOH generation column. The applied current was varied from 1.0 to 70 mA and the operating voltage was monitored. The carrier flow rate was maintained at 2.0 mL/minute.

Figure 18:
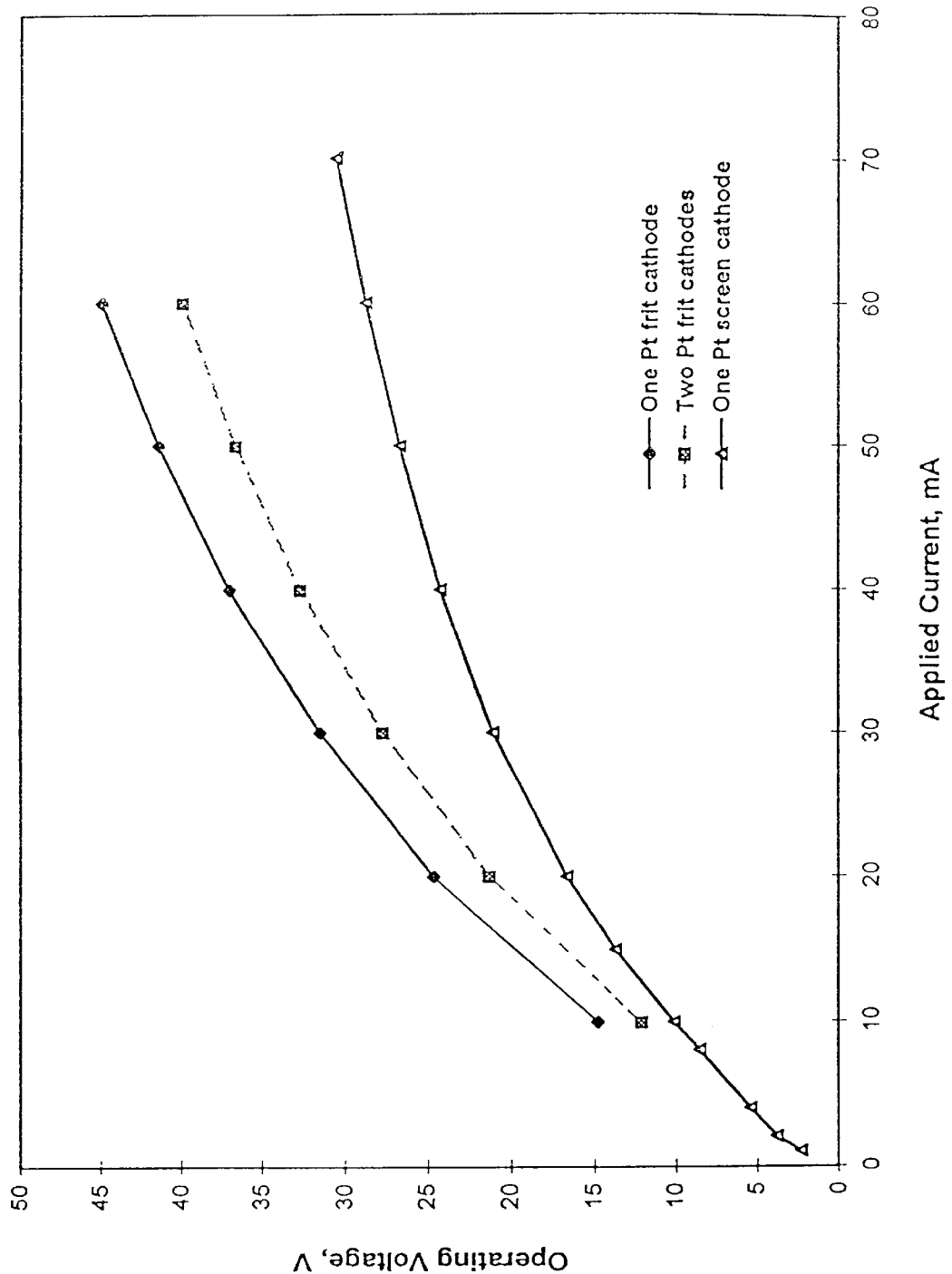

The dependence of the operating voltage on the applied current determined for the KOH generator operated in three cathode configurations is shown in FIG. 18. At an applied current of 60 mA, the operating voltage was 45 V when one porous Pt frit was used as the cathode, 40 V when two porous Pt frits were used as the cathodes, and 29 V when the cathode was made of a Pt screen formed to wrap around the resin bed. The results indicate that the operating voltage of the KOH generator can be decreased significantly by increasing the contact area between the ion exchange resin and the electrode, so that KOH at relatively high concentrations can be generated without being limited by excessive heating.

EXAMPLE 7

On-line high pressure removal of hydrogen gas.

An on-line high pressure gas permeable removal device was constructed according to the design shown in FIG. 9. A polymeric tubing (0.020-inch OD×0.010-inch ID×1.0 meter length) obtained from Biogeneral Inc. (San Diego, Calif.) was used as the gas permeable tubing in the device. The device was tested for removing hydrogen gas in the KOH solution generated at applied currents up to 160 mA using the large capacity KOH generator described in Example 4. The carrier flow rate for the generator was 2.0 mL/minute. In some experiments, the outlet of the device was connected to a piece of 0.005-inch ID PEEK tubing that generated a pressure drop of 1400 psi at 2.0 mL/min; the PEEK tubing outlet was immersed in the deionized water in a small, clear glass vial, and the presence of hydrogen gas in the KOH solution was visually monitored (by observing the formation of gas bubbles). In some experiments, the KOH generator and gas removal device were installed in an ion chromatography system as shown in FIG. 10, the baseline noise of the conductivity detector was monitored, and the flow of chromatography system effluent was used to shield the outside of the gas permeable tubing to remove the released hydrogen gas and prevent the readsorption of carbon dioxide from the ambient air, as shown in FIG. 9.

Figure 19:
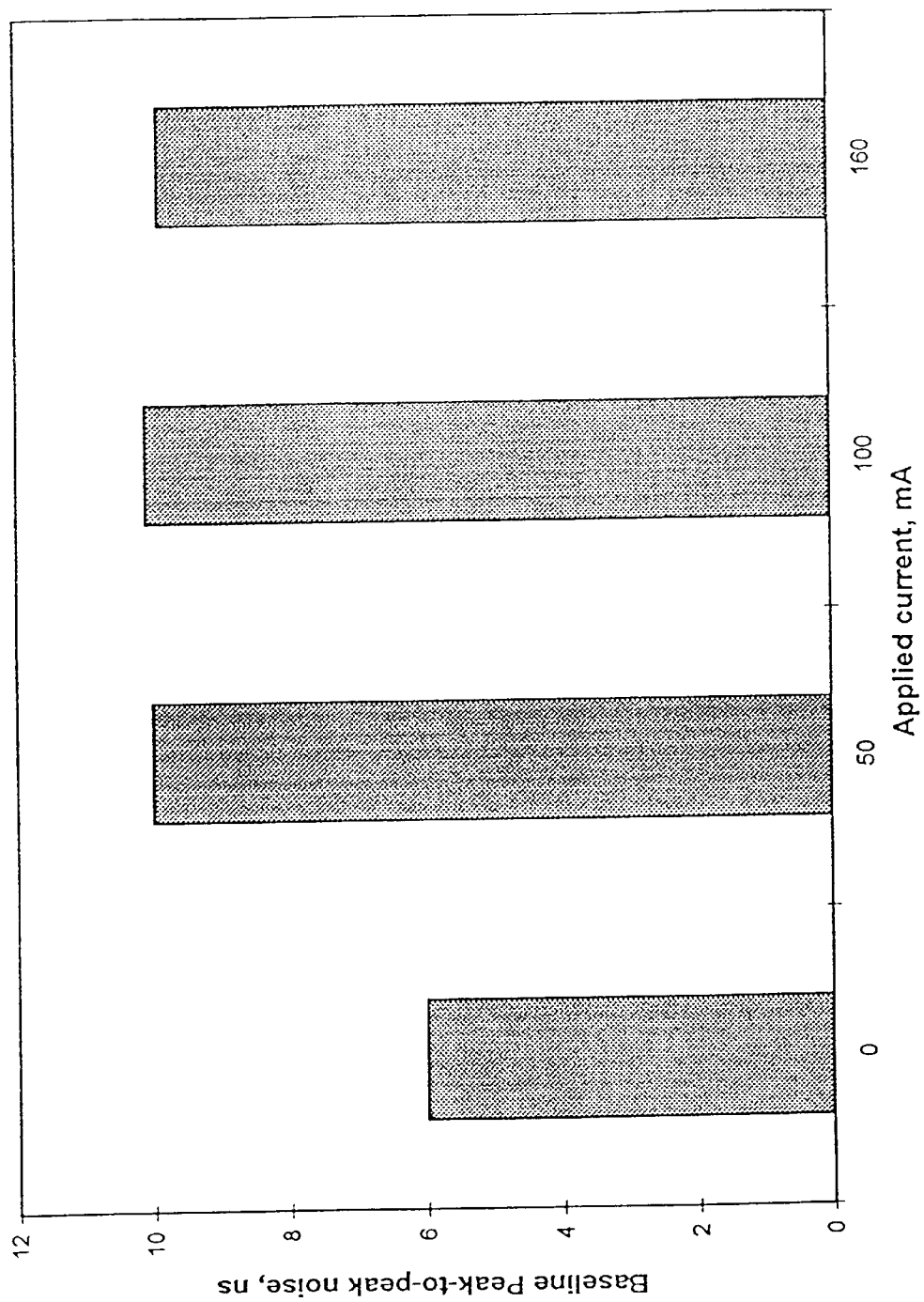

The on-line high pressure gas removal device was highly effective in removing the hydrogen gas. No hydrogen gas bubbles could be visually observed in the KOH solution generated at applied currents up to 160 mA. FIG. 19 shows the baseline peak-to-peak noises measured at different currents obtained using the device; they are similar to those obtained with the conventional ion chromatography system. At the applied current of 160 mA, hydrogen gas is generated at a rate of about 1.1 mL/min (gas volume at 14.7 psi). Therefore, the gas removal efficiency of the device was quite

EXAMPLE 8

Use of a large capacity KOH generator in isocratic and gradient separation of common anions by ion chromatography.

An ion chromatography system consisting of a large capacity KOH generator, an on-line high pressure gas removal device, and common Dionex ion chromatography system components was assembled as shown in FIG. 10. The large capacity KOH generator used was similar to the one described in Example 3. The on-line high pressure gas removal device described in Example 7 was used. A Dionex AS 11 column (4-mm ID×250-mm length) was used as the analytical separation column. In isocratic separation experiments, the large capacity KOH generator was applied with a constant current of 40 mA to generate 12.4 mM KOH at 2.0 mL/minute. In gradient separation experiments, the current applied to the large capacity KOH generator was changed from 2.0 to 50 mA in steps of 0.5 mA per 20 seconds to generate a gradient of KOH from 0.6 to 15.5 mM at 2.0 mL/minute.

Figure 20:
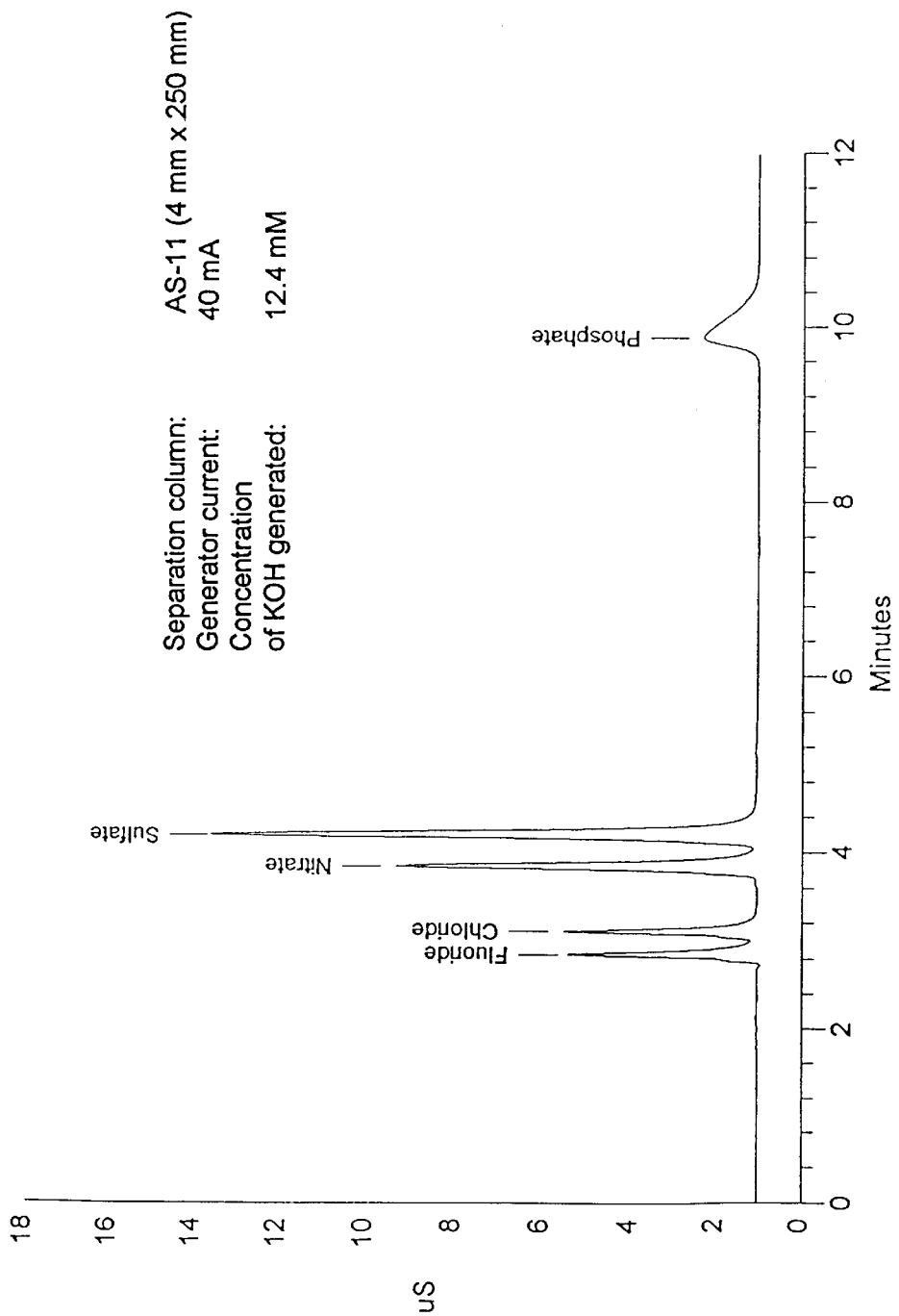
Figure 21:
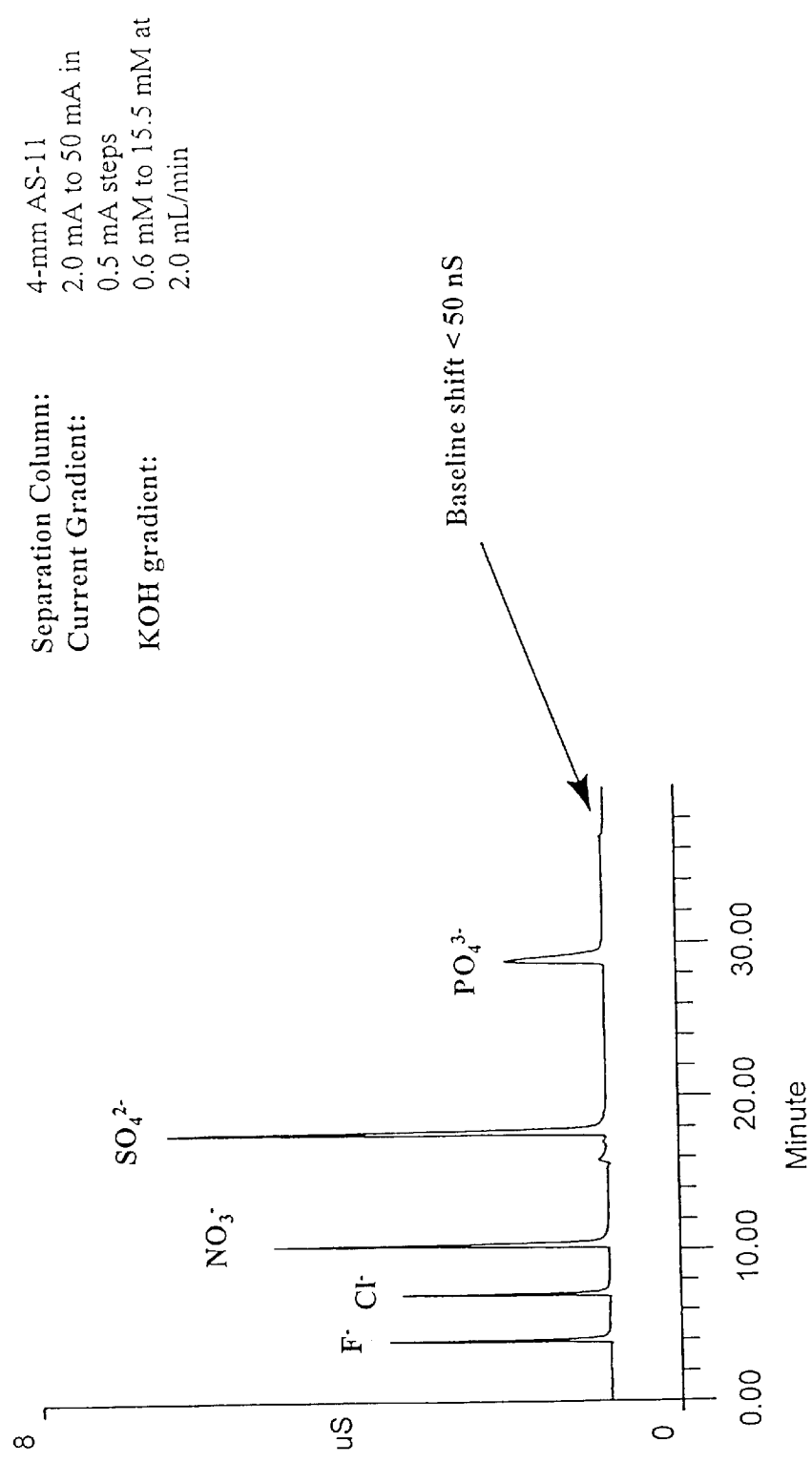
Figure 22:
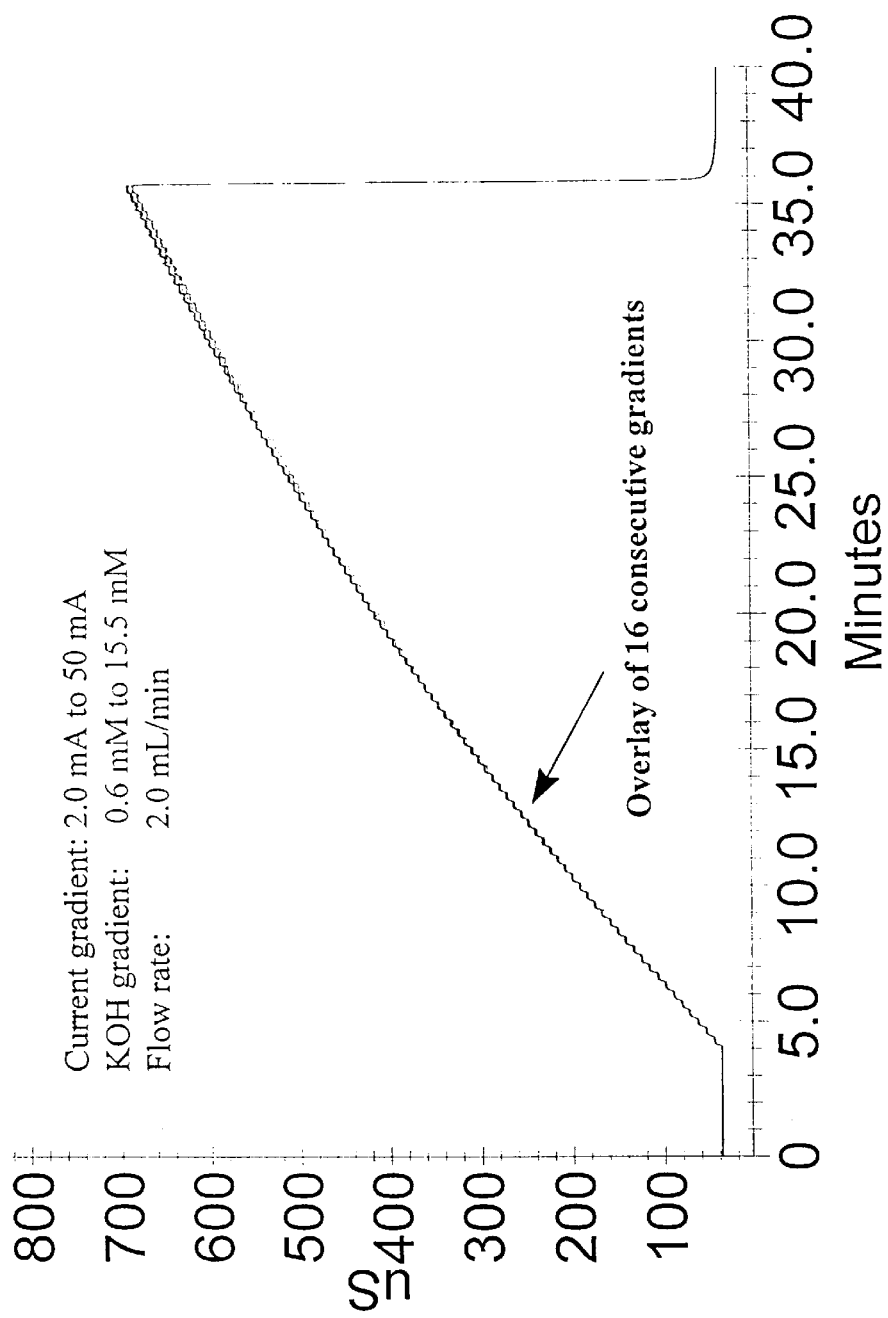

FIG. 20 and 21 show, respectively, the representative isocratic and gradient separation of fluoride, chloride, nitrate, sulfate, and phosphate. FIG. 22 shows the reproducible overlay of 16 consecutive KOH gradients generated using the large capacity KOH generator. It is worthy to point out that the chromatographic baseline shift during the KOH gradient was less than 50 nS in the chromatogram shown in FIG. 21. If the same hydroxide gradient is generated using a conventional gradient pump, the baseline shift is usually about 500 to 1500 nS. These results demonstrate that the high purity KOH solutions can be generated reproducibly using the large capacity KOH generator, and used effectively as eluents in ion chromatography. The results also suggest that the performance of an ion chromatography method can be enhanced because the use of high purity hydroxide solution generated on-line results in minimal baseline shifts during gradient separation, as illustrated in the next example.

EXAMPLE 9

Use of a large capacity KOH generator in determination of trace anions in high purity water by ion chromatography.

Figure 23:
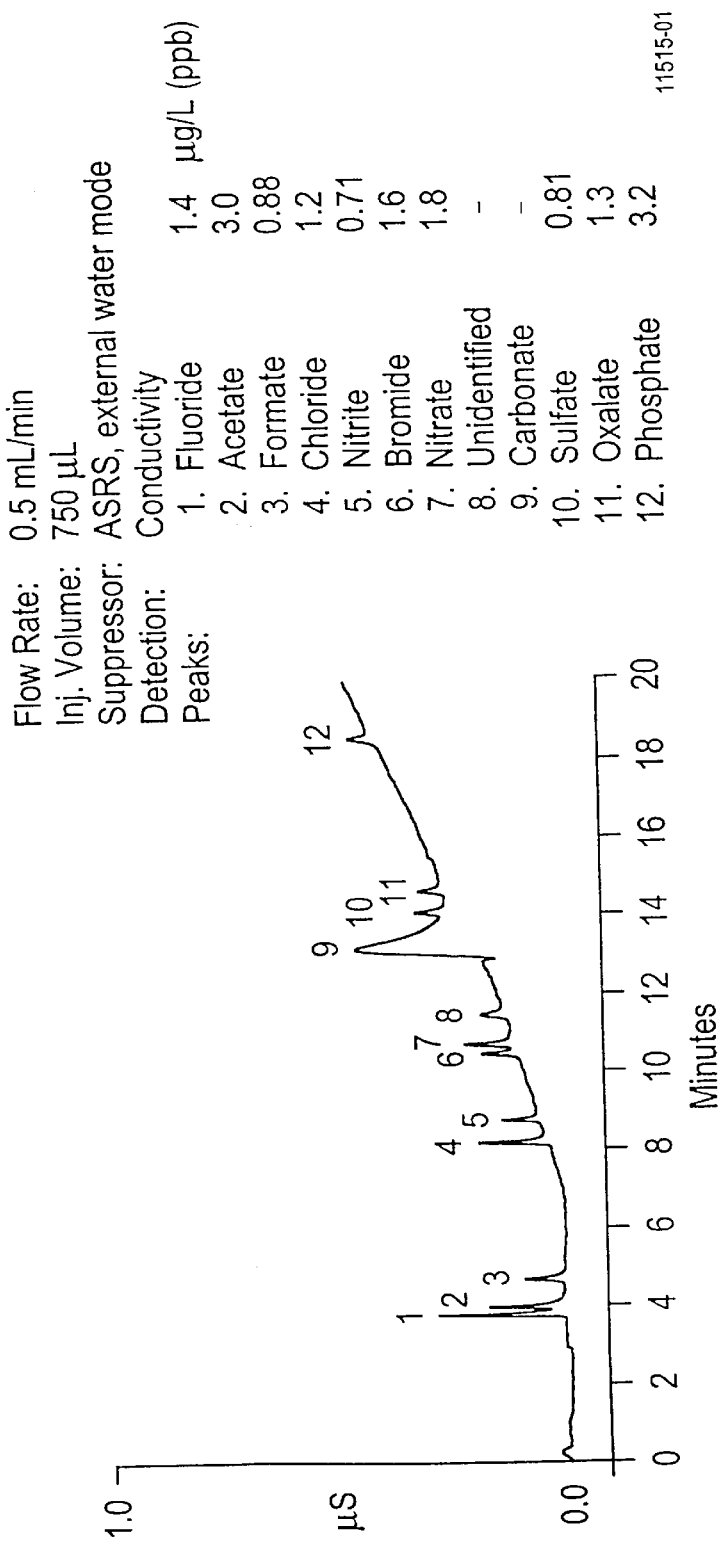

Dionex Application Note 113 describes a method for determination of trace anions in high purity waters. In this method, the large volume direction injection technique is used (sample loop is 750 $\mu$L), target anions are separated on a Dionex microbore AS 11 column (2-mm ID×250-mm length) using a NaOH gradient. FIG. 23 shows the typical chromatogram obtained when the NaOH gradient (0.5 to 26 mM NaOH) was generated using a gradient pump and NaOH solutions prepared by conventional means. The baseline shift is about 500 nS during the gradient. The baseline shift occurs because NaOH solutions are easily contaminated with carbon dioxide in the ambient air during the solution preparation and use, even with precautions.

To demonstrate the benefits of using high purity KOH eluent generated by the large capacity KOH generator, an ion chromatography system similar to the one used in Example 8 was assembled. A Dionex microbore AS-11 column was used as the analytical separation column. The current applied to the large capacity KOH generator was changed from 0.4 to 21 mA in steps of 0.4 mA per 17 seconds to generate a gradient of KOH from 0.5 to 26 mM at 0.5 mL/minute.

Figure 24:
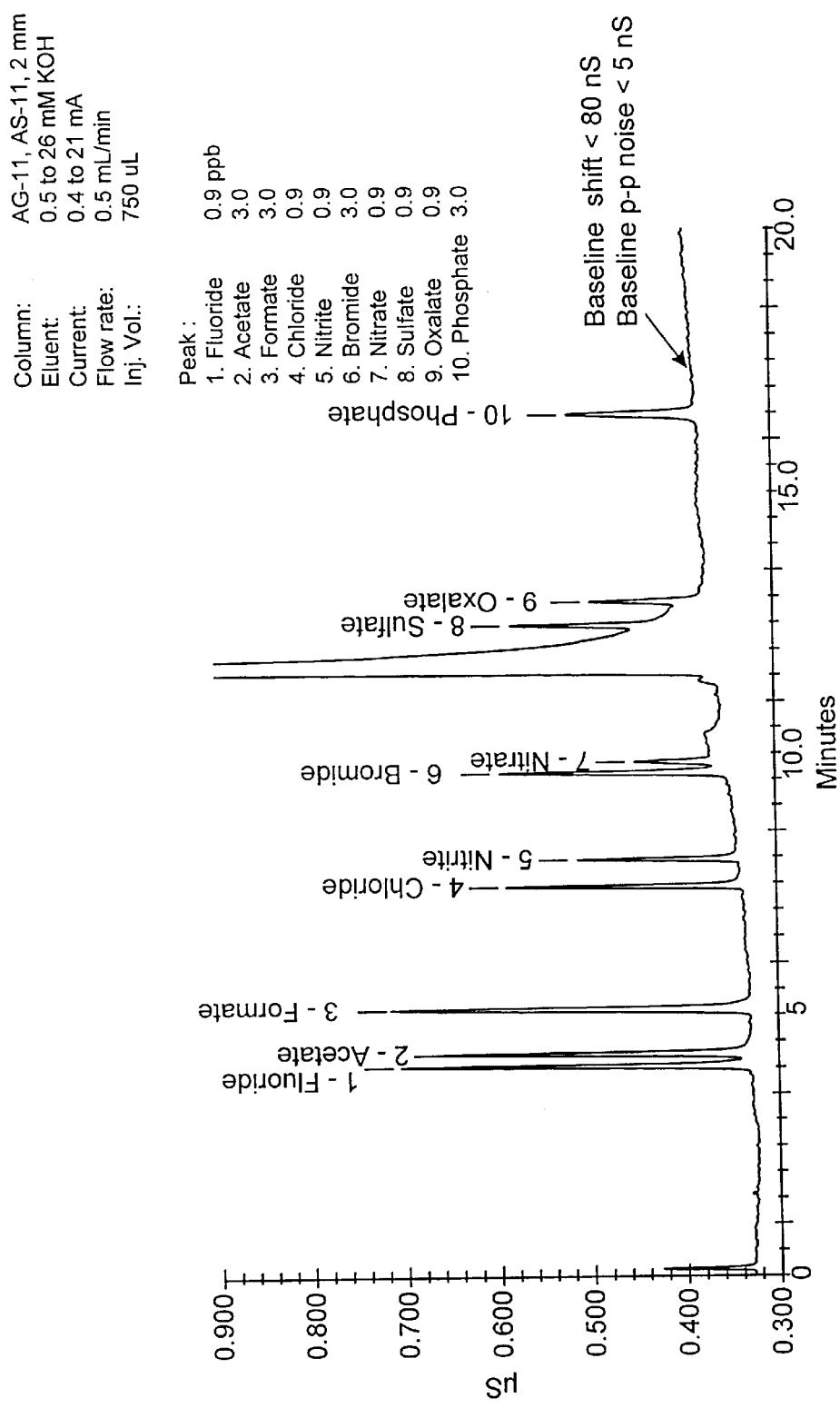

FIG. 24 shows a representative chromatogram obtained for a sample of deionized water spiked with 10 anions at levels of 0.9 to 3.0 ppb. Since the KOH solution generated with the large capacity KOH generator was essentially free of carbonate contamination, the observed baseline shift was less than 80 nS during the gradient. The significantly smaller baseline shift during the gradient achieved using the KOH generator leads to improvements in the method performance. These results suggest that the performance of an ion chromatography method can be enhanced by using a large capacity KOH generator.

EXAMPLE 10

Generation of methanesulfonic acid (MSA) using a large capacity MSA generator employing a large capacity $CH_3SO_3^-$ ion supply reservoir.

Figure 25:
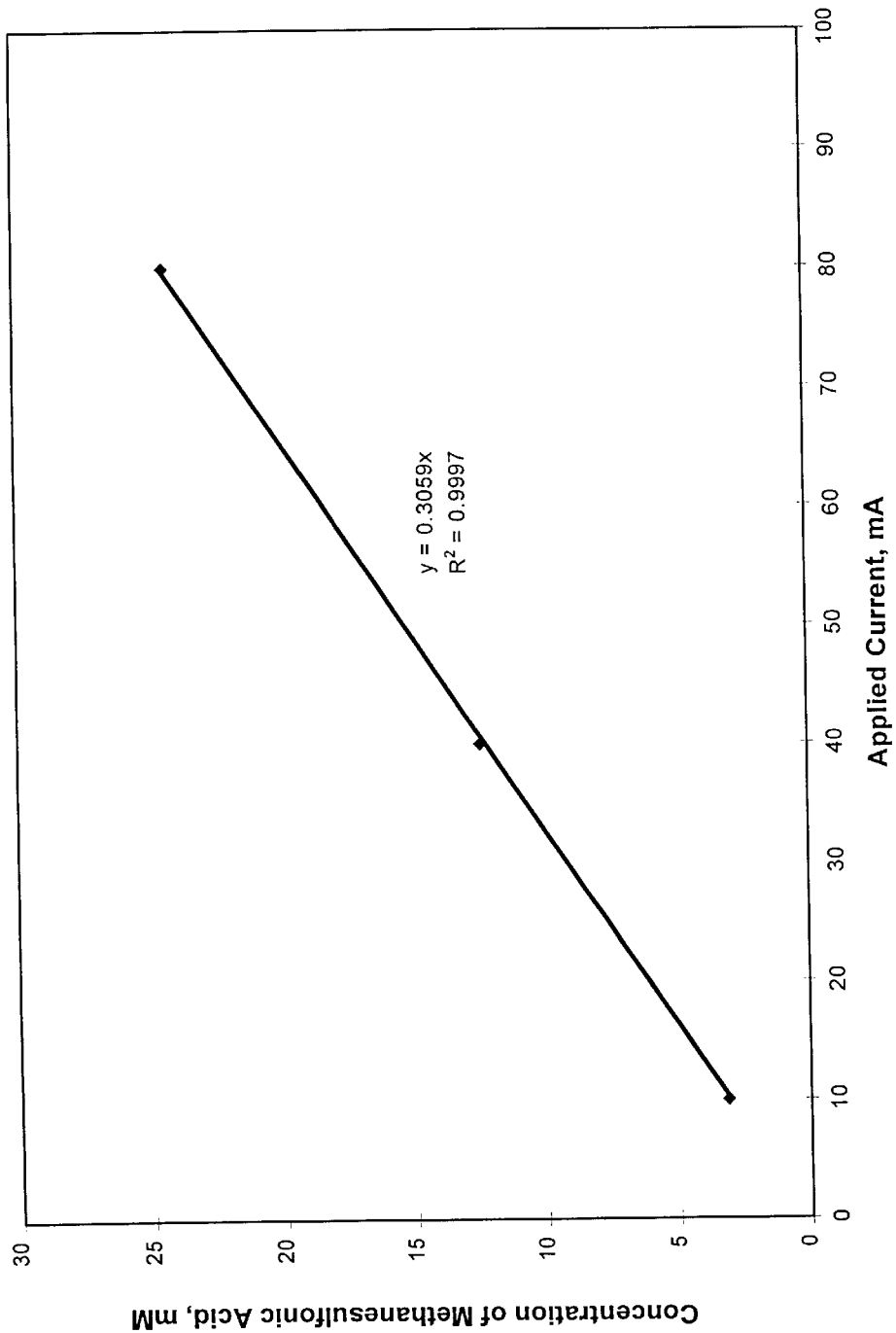
Figure 26:
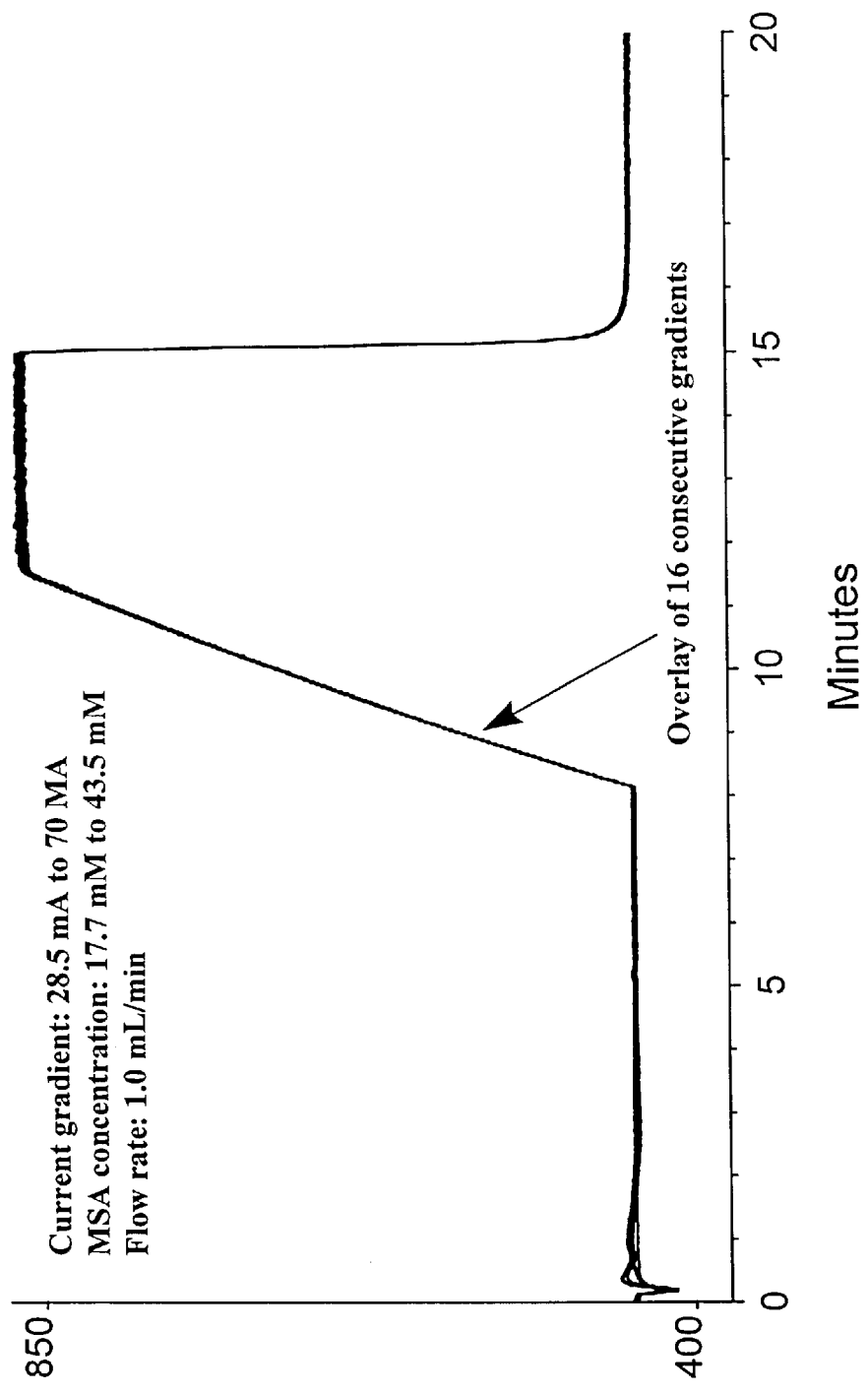

A large capacity MSA generator employing a $CH_3SO_3^-$ ion supply reservoir was constructed to evaluate this preferred embodiment of the invention. The MSA generation column (7-mm ID×10-mm length) was packed with a 20-$\mu$m, 8% cross-link strongly basic (quaternary amine functional groups) styrene/divinyl benzene resin in $CH_3SO_3^-$ form and equipped with a Pt screen cathode. The $CH_3SO_3^-$ ion supply reservoir was filled with a 2.0 M $NH_4CH_3SO_3$ solution. The large capacity MSA generator was used to generate MSA solutions at applied currents ranging from 10 to 100 mA and a carrier flow rate of 1.0 or 2.0 mL/min. The operating voltage for the large capacity MSA generator was 9.5 V at 10 mA, 30 V at 50 mA, and 38.5 V at 100 mA. The concentrations of MSA generated at 10, 40, and 80 mA were determined by titration using a 10-mM NaOH standard. FIG. 25 shows that there was excellent correlation ($R^2$=0.9997) between the applied current and the determined concentration of MSA generated. In some experiments, the current applied to the large capacity MSA generator was changed from 28.5 mA to 70 mA in steps of 1.0 mA per 5 seconds to generate a gradient of MSA from 17.7 mM to 43.5 mM at 1.0 mL/min. FIG. 26 shows the reproducible overlay of 16 consecutive MSA gradients generated using the large capacity MSA generator. These results indicate that the large capacity MSA generator can be used to generate MSA at desired concentrations accurately and reproducibly.

EXAMPLE 11

Use of the large capacity MSA generator in the separation of cations by ion chromatography.

An ion chromatography system consisting of a large capacity MSA generator, an on-line high pressure gas removal device, and common Dionex ion chromatography system components was assembled. The large capacity MSA generator described in Example 10 was used. The on-line high pressure gas removal device described in Example 7 was used. A Dionex CS12A column (4-mm ID×250-mm length) was used as the analytical separation column. The current applied to the large capacity MSA generator was changed from 28.5 mA to 70 mA in steps of 1.0 mA per 5 seconds to generate a gradient of MSA from 17.7 mM to 43.5 mM at 1.0 mL/min. In some experiments, MSA gradients from 17.7 mM to 43.5 mM at 1.0 mL/min were generated by using a Dionex GP40 gradient pump with deionized water and a 100 mM MSA solution prepared from reagent grade MSA.

Figure 27:
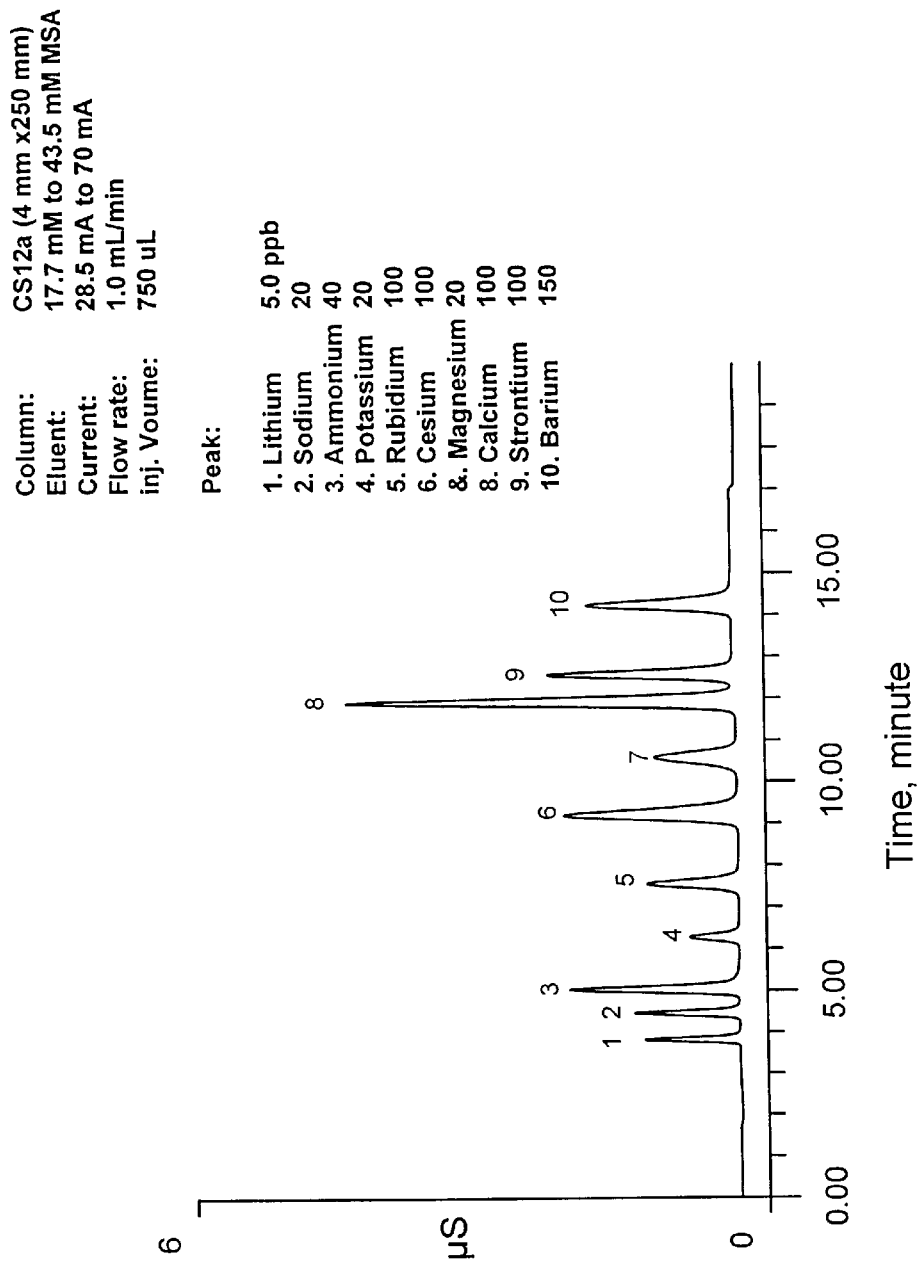
Figure 28:
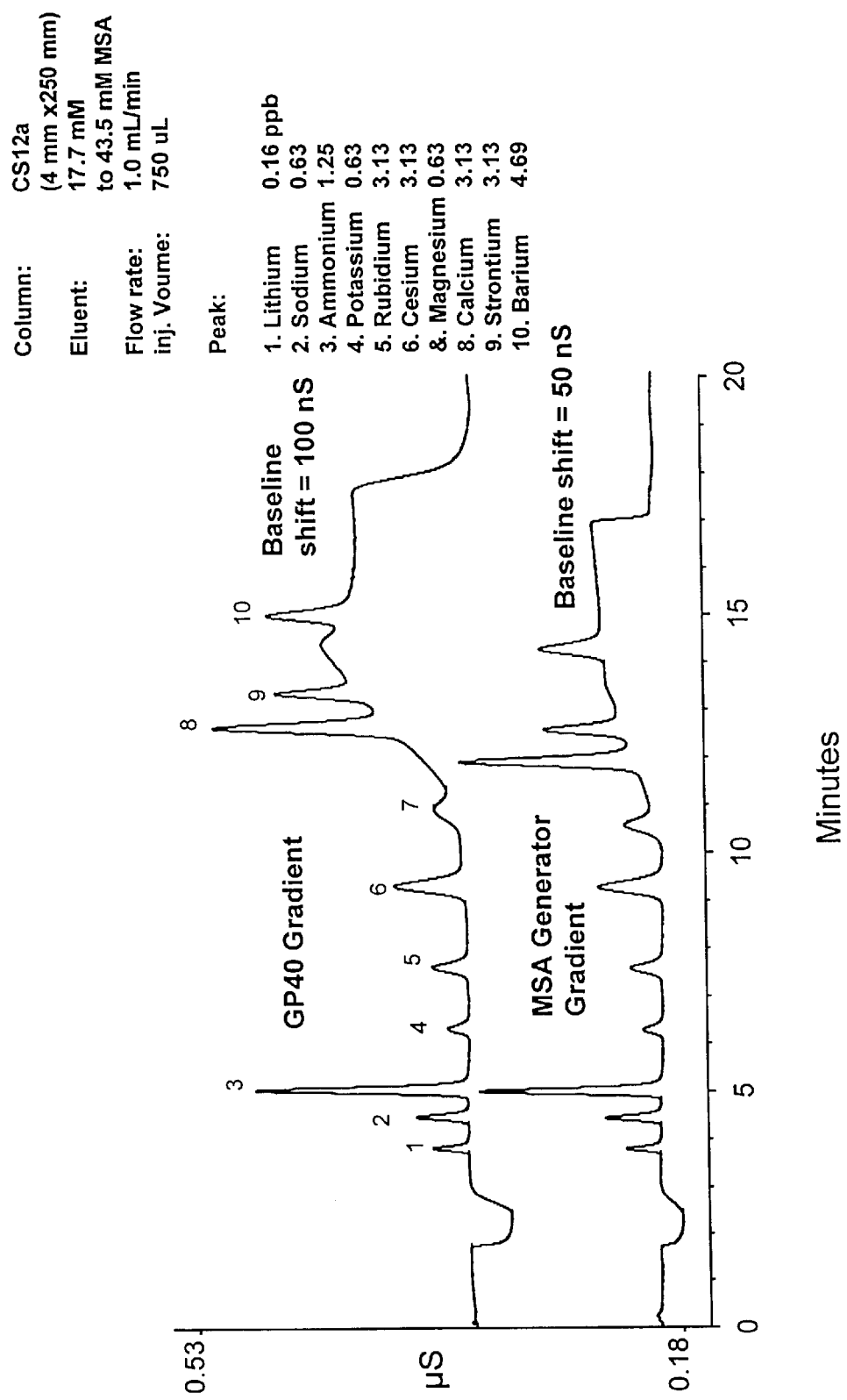

FIG. 27 shows a representative gradient separation of 10 cations using the MSA gradient generated using the large capacity MSA generator. FIG. 28 shows the overlay of two representative chromatograms obtained for a high purity water sample spiked with 10 cations at sub to low µg/L levels, using identical MSA gradients generated with either the large capacity MSA generator or the GP40 gradient pump. The results show that the MSA generator gradient yielded lower detector background and smaller baseline shift during the gradient than the GP40 pump gradient. These improvements can be attributed to the fact that the MSA solution generated using the large capacity MSA generated is of high purity and free of contaminants that may be present in the reagent grade MSA.

Figure 29:
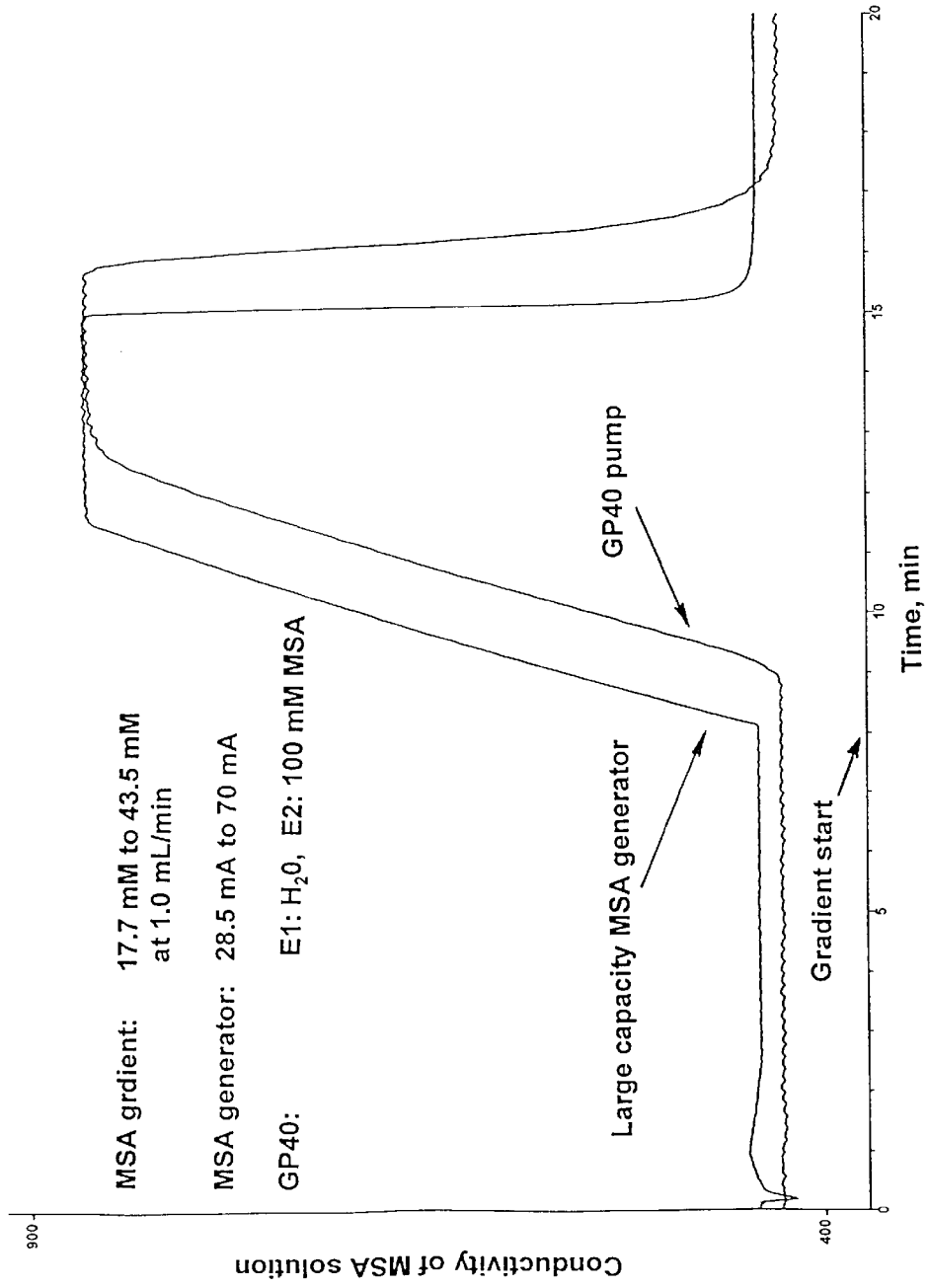

The results also show that the elution of calcium, strontium, and barium were delayed about one minute in the chromatogram obtained using the GP40 pump gradient when compared to the chromatogram obtained using the MSA generator gradient. In the ion chromatography system employing the large capacity MSA generator and the on-line high pressure gas removal device, the total dead volume of the two device was less than 0.1 mL. On the other hand, the GP40 gradient pump used had a total dead volume (consisted of dead volumes in proportioning valves and pump heads) of about 1.0 mL. FIG. 29 shows the comparison of MSA gradients generated using the large capacity MSA generator and the GP40 gradient pump. The results show that the profile of the MSA generator gradient had minimal delay in the MSA gradient while noticeable gradient delay was observed when the GP40 gradient pump was used.

What is claimed is:

1. An apparatus for generating an acid or base comprising:
    (a) an ion source reservoir containing a source of either anions or cations,
    (b) an acid or base generation chamber having inlet and outlet ports, the volume of said ion source reservoir being at least about 5 times the volume of said acid or base generation chamber,
    (c) a charged first barrier disposed between said ion source reservoir and said acid or base generation chamber, said barrier substantially preventing liquid flow while providing an ion transport bridge for only ions of one charge, positive or negative,
    (d) a first electrode in electrical communication with said ion source reservoir,
    (e) a second electrode in electrical communication with said first acid or base generation chamber, and
    (f) an aqueous liquid source in fluid communication with said acid or base generation chamber inlet port.

2. The apparatus of claim 1, further comprising:
    (g) a power supply for applying an electrical potential between said first and second electrodes.

3. The apparatus of claim 1, in which said acid or base generated in said acid or base generation chamber is used as an eluent stream for analysis of samples containing components of interest, said apparatus further comprising:
    (g) a sample injection port for injecting a liquid sample stream of ions to be detected,
    (h) a chromatographic separator for separating said components of interest, and having inlet and outlet ports, said inlet port being in fluid communication with said sample injection port and said acid or base generator outlet port, whereby a chromatography effluent exits from said outlet port, and
    (i) a detector in fluid communication with said chromatographic separator for detecting the separated components of interest in said chromatography effluent.

4. The apparatus of claim 1 further comprising:
    (g) a gradient pump for pumping one or more gradient eluents into said ion-containing solution generated in said first acid or base generation chamber.

5. The apparatus of claim 1 further comprising:
    (g) a flow restrictor in fluid communication with the outlet of said first acid or base generation chamber outlet port.

6. The apparatus of claim 1, further comprising:
    (g) a bed of ion exchange resin with exchangeable ions of the same charge as said first barrier disposed in said generation chamber between said first barrier and said second electrode and providing an ion path therebetween.

7. The apparatus of claim 1, further comprising:
    (g) a charged screen of the same charge as said first barrier disposed between said first barrier and said second electrode in said generation chamber and providing an ion path therebetween.

8. The apparatus of claim 1, further comprising an uncharged screen between said first barrier and said second electrode in said generation chamber.

9. The apparatus of claim 1 in which said charged first barrier has a thickness at least equal to a stack of ion exchange membranes.

* * * * *

UNITED STATES PATENT AND TRADEMARK OFFICE
CERTIFICATE OF CORRECTION

PATENT NO. : 6,682,701 B1
DATED : January 27, 2004
INVENTOR(S) : Yan Liu et al.

It is certified that error appears in the above-identified patent and that said Letters Patent is hereby corrected as shown below:

<u>Column 5,</u>
Line 19, delete equation (2), and insert the following corrected equation (2):
-- $2 H_2O + 2e^- \rightarrow 2OH^- + H_2$ (2) --

<u>Column 9,</u>
Line 20, change "4,000 mmeq" to -- 4,000 meq --.

<u>Column 15,</u>
Lines 8 and 9, change "(18-mm ID-185-mm length)" to -- (18-mm IDX185-mm length --.

Signed and Sealed this

First Day of June, 2004

JON W. DUDAS
*Acting Director of the United States Patent and Trademark Office*